US008362210B2

(12) United States Patent
Lazar et al.

(10) Patent No.: US 8,362,210 B2
(45) Date of Patent: Jan. 29, 2013

(54) ANTIBODY VARIANTS WITH ENHANCED COMPLEMENT ACTIVITY

(75) Inventors: Gregory A. Lazar, Arcadia, CA (US); Sher Bahadur Karki, Pomona, CA (US); Gregory L. Moore, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 107 days.

(21) Appl. No.: 13/009,820

(22) Filed: Jan. 19, 2011

(65) Prior Publication Data

US 2011/0236375 A1 Sep. 29, 2011

Related U.S. Application Data

(60) Provisional application No. 61/296,316, filed on Jan. 19, 2010.

(51) Int. Cl.
| | |
|---|---|
| C07K 16/00 | (2006.01) |
| C12P 21/08 | (2006.01) |
| A61K 39/395 | (2006.01) |
| A61K 39/40 | (2006.01) |
| A61K 39/42 | (2006.01) |
| C07K 1/00 | (2006.01) |

(52) U.S. Cl. ............... 530/387.1; 530/387.3; 530/387.7; 530/388.1; 530/388.15; 530/388.22; 530/388.23; 424/130.1; 424/132.1; 424/133.1; 424/134.1; 424/141.1; 424/142.1; 424/143.1; 424/144.1; 424/145.1; 424/152.1; 424/153.1; 424/156.1; 424/158.1

(58) Field of Classification Search .................. None
See application file for complete search history.

(56) References Cited

U.S. PATENT DOCUMENTS 5,693,762 A 12/1997 Queen et al.

FOREIGN PATENT DOCUMENTS

| WO | WO 92/11018 | 7/1992 |
|---|---|---|
| WO | WO 2006/019447 A1 | 2/2006 |
| WO | WO 2006/047350 A2 | 5/2006 |
| WO | WO 2006/105338 A2 | 10/2006 |
| WO | WO 2008/150494 A1 | 12/2008 |
| WO | WO 2011/028592 A1 | 3/2011 |

OTHER PUBLICATIONS

Lazar, G. et al., "Engineered antibody Fc variants with enhanced effector function", PNAS, vol. 103, No. 11, pp. 4005-4010 (2006).
Moore, G. et al., "Engineered Fc variant antibodies with enhanced ability to recruit complement and mediate effector functions", MABS, Landes Bioscience, US, vol. 2, No. 2, ps. 181-189 (2010).
Tao, M. H., et al., "Structural features of human immunoglobulin G that determine", The Journal of Exp. Medicine, vol. 178, No. 2, pp. 661-667 (1993).
Miletic, V.D. et al., "Complement-immunoglobulin interactions" Current Opinion in Immunology, vol. 7, No. 1, pp. 41-47 (1995).
Desjarlais, John, et al., "Modulation of antibody effector function", Expermiental Cell Research, vol. 317, No. 9, pp. 1278-1285 (2011).
U.S. Appl. No. 10/672,280, filed Sep. 26, 2003, Lazar, et al.
U.S. Appl. No. 10/822,231, filed Mar. 26, 2004, Lazar, et al.
U.S. Appl. No. 11/004,590, filed Dec. 3, 2004, Lazar, et al.
U.S. Appl. No. 11/124,620, filed May 5, 2005, Lazar, et al.
U.S. Appl. No. 11/174,287, filed Jun. 30, 2005, Dahiyat, et al.
U.S. Appl. No. 11/256,060, filed Oct. 21, 2005, Lazar, et al.
U.S. Appl. No. 11/274,065, filed Nov. 14, 2005, Chamberlain, et al.
U.S. Appl. No. 11/396,495, filed Mar. 31, 2006, Lazar, et al.
U.S. Appl. No. 11/436,266, filed May 17, 2006, Chamberlain, et al.
U.S. Appl. No. 11/538,406, filed Oct. 3, 2006, Desjarlais, et al.
U.S. Appl. No. 11/538,411, filed Oct. 3, 2006, Desjarlais, et al.
U.S. Appl. No. 11/932,151, filed Oct. 31, 2007, Chamberlain, et al.
U.S. Appl. No. 12/020,443, filed Jan. 25, 2008, Lazar, et al.
U.S. Appl. No. 12/341,769, filed Dec. 22, 2008, Chamberlain, et al.
U.S. Appl. No. 12/434,533, filed May 1, 2009, Alley, et al.
Alley, S.C., et al., "Antibody-Drug Conjugates: Targeted Drug Delivery for Cancer" Curr Opin Chem Biol 14[4]:529-537 (2010).
Ashkenazi, A. and S.M. Chamow, "Immunoadhesins As Research Tools and Therapeutic Agents," Curr. Opin. Immunol. (9)195-200 (1997).
Campbell, C. and P. Stanley, "A Dominant Mutation to Ricin Resistance in Chinese Hamster Ovary Cells Induces UDP-GlcNAc:Glycopeptide β-4-N-Acetylglucosaminyltransferase III Activity," J. Biol. Chem. 261(21):13370-13378 (1984).
Carter, P.J., "Potent Antibody Therapeutics by Design,",Nature Reviews Immunology, 6:343-357 (2006).
Chamow, S.M. and A. Ashkenazi, "Immunoadhesins: Principles and Applications," TIBTECH (14)52-60 (1996).
Chan, A.C. and P.J. Carter, "Therapeutic Antibodies for Autoimmunity and Inflammation" Nature Reviews Immunology, 10:301-316 (2010).
Clark, M.R., "Chemical Immunology Antibody Engineering IgG Effector Mechanisms," Dissertation submitted to Immmunology Div of Dept of Pathology, Cambridge University, UK J. Chem. Immunol. (65) 88-110 (1997).
Cox, K.M. et al., "Glycan optimization of a Human Monoclonal Antibody in the Aquatic Plant Lemna minor," Nat Biotechnol 24[12]:1591-1597 (2006).
Dall'Acqua, W.F. et al., "Increasing the Affinity A Human IgG1 for the Neonatal Fc Receptor: Biological Consequences," J. Immunol. (169) 5171-5180 (2002).
Dall'Acqua, W.F., et al., "Biological Consequences IgG1 for the Neonatal Fc Receptor: Increasing the Affinity of a Human," J Biol Chem, 281:23514-23524 (2006).
Davies, J. et al., "Expression of GnTIII in a Recombinant Anti-CD20 CHO Production Cell Line: Expression of Antibodies With Altered Glycoforms Leads to an Increase in ADCC Through Higher Affinity to FcγRIII," Biotech and Bioeng 74(4) 288-294 (2001).

(Continued)

Primary Examiner — Chun Dahle
(74) Attorney, Agent, or Firm — Morgan Lewis & Bockius LLP; Robin M. Silva, Esq.; Ada O. Wong, Esq.

(57) ABSTRACT

The present invention relates to novel Fc variants that comprise at least one novel amino acid residue which may provide for enhanced effector function. More specifically, this invention provides Fc variants that have modified binding affinity to one or more Fc receptor or ligand (e.g., Fc gamma R, C1q). Additionally, the Fc variants have altered complement dependent cytotoxicity (CDC) activity and/or antibody-dependent cell-mediated cytotoxicity (ADCC). The invention further provides methods and protocols for the application of said Fc variants, particularly for therapeutic purposes.

10 Claims, 11 Drawing Sheets

OTHER PUBLICATIONS

Dechant, M. et al., "Complement-Dependent Tumor Cell Lysis Triggered by Combinations of Epidermal Growth Factor Receptor Antibodies," *Cancer Res.* 68(13): 4998-5003 (2008).

Durocher, Y. et al, "High-Level and High-Throughput Recombinant Protein Production by Transient Transfection of Suspension-Growing Human 293-EBNA1 Cells," *Nucleic Acids Research*, 30[2]:E9 (2002).

Edelman, et al., "The Covalent Structure of an Entire yG Immunoglobulin Molecule," *Biochemistry* (63) 78-85 (1969).

Gasque, Philippe, "Complement: A Unique Innate Immune Sensor for Danger Signals," *Mol. Immunol.* 41:1089-1098 (2004).

Gelderman, K.A., et al., "Complement Function in mAb-Mediated Cancer Immunotherapy," *Trends in Immunol.* 25(3): 158-164 (2004).

Ghetie, V. and E.S. Ward, "Multiple Roles for the Major Histocompatibility Complex Class I-Related Receptor FcRn," *Annu. Rev. Immunol.* (18) 739-766 (2000).

Gorman, S.D. and M.R. Clark, "Humanisation of Monoclonal Antibodies for Therapy," *Semin Immunol*, 2[6]:457-66 (1990).

Hayhurst, A. and G. Georgiou, "High-Throughput Antibody Isolation," *Curr. Opin. Chem. Biol.* (5)683-689 (2001).

Hinton, P.R. et al., "Engineering Human IgG Antibodies With Longer Serum Half-Lives in Primates," *J. Biol. Chem.*, 279(8): 6213-6216 (2004).

Hinton, P.R., et al., "An Engineered Human IgG1 Antibody with Longer Serum Half-Life," *J Immunol*, 176:346-356 (2006).

Holliger, P. et al., "Diabodies: Small bivalent and bispecific antibody fragments," *Proc Natl Acad Sci USA*, 990:6444-6448 (1993).

Holliger, P and P.J. Hudson, "Engineered Antibody Fragments and the Rise of Single Domains," *Nature Biotechnology*, 23[9]:1126-1136 (2005).

Horton, H. et al., "Potent In vitro and In vivo Activity of an Fc-Engineered Anti-CD19 Monoclonal Antibody Against Lymphoma and Leukemia," *Cancer Res* 68(19): 8049-8057 (2008).

Huang, C., "Receptor-Fc fusion therapeutics, traps, and MIMETIBODY™ Technology", *Curr Opin Biotechnol*, 20[6]:692-699 (2009).

Hubbard, S.C. et al., "Synthesis and Processing of Aspargine-Linked Oligosaccharides," *Ann Rev Biochem*, 50:555-583 (1981).

Jefferis, R. et al., "Interaction Sites on Human IgG-Fc for FcyR: Current Models," *Immunol. Lett.* 82(1): 57-65 (2002).

Jones, P.T. et al., "Replacing the Complementarity-Determining Regions in a Human Antibody With Those of a Mouse," *Nature*, 321:522-525 (1986).

Kaneko, Y. et al., "Anti-Inflammatory Activity of Immunoglobulin G Resulting from Fc Sialylation," *Science*, 313:670-673 (2006).

Kim, T.D. et al., "Analysis of FcyRIII and IgG Fc Polymorphism Reveals Functional and Evolutionary Implications of Protein-Protein Interaction," *J. Mol. Evol.* (53)1-9 (2001).

Koho, H. et al., "Monoclonal Antibodies to Antigens Associated With Transitional Cell Carcinoma of the Human Urinary Bladder," *Cancer Immunol. Immunotherapy* 17:165-172 (1984).

Lazar, G.A. et al., "A Molecular Immunology Approach to antibody Humanization and Functional Optimization," *Mol Immunol*, 44:1986-1998 (2007).

Lefranc, G. et al., "Gm, Am and Km Immunoglobulin Allotypes of Two Populations in Tunisia," *Hum Genet*, 50:199-211 (1979).

Li, H. et al., "Optimization of Humanized IgGs in Glycoengineered *Pichia pastoris*," *Nature Biotechnol*, 24[2]:210-215 (2006).

Liu, C.C. and P.G. Schultz, "Adding New Chemistries to the Genetic Code," *Annu Rev Biochem*, 79:413-444 (2010).

Lonberg, N., "Fully human antibodies from transgenic mouse and phage display platforms," *Curr Opin Immunol*, 20[4]:450-459 (2008).

Macor, P. and F. Tedesco, "Complement As Effector System in Cancer Immunotherapy," *Immunol. Lett.* (111): 6-13 (2007).

Maynard, J. and G. Georgiou, "Antibody Engineering," *Annu Rev Biomed Eng*, 2:339-376 (2000).

Meeker, T.C. et al., "A Unique Human B Lymphocyte Antigen Defined by a Monoclonal Antibody," *Hybridoma* 3(4):305-320 (1984).

Mejias, A., et al., "Comparative Effects of Two Neutralizing Anti-Respiratory Syncytial Virus (RSV) Monoclonal Antibodies in the RSV Murine Model: Time Versus Potency," *Antimicrob Agents Chemother*. 49(11): 4700-4707 (2005).

Mondon, P. et al., "Human antibody libraries: A race to engineer and explore a larger diversity," *Front Biosci*, 13:1117-1129 (2008).

Morea, V.et al., "Antibody structure, Prediction and Redesign," *Biophys Chem*, 68:9-16 (1997).

Morea, V. et al., "Antibody Modeling: Implications for Engineering and Design," *Methods*, 20:267:279 (2000).

Natsume, A. et al., "Engineered Antibodies of IgG1/IgG3 Mixed Isotype With Enhanced Cytotoxic Activities," *Cancer Res.* 68(10) 3863-3871 (2008).

Nechansky, A. et al., "Compensation of endogenous IgG mediated inhibition of antibody-dependent cellular cytotoxicity by glycol-engineering of therapeutic antibodies," *Mol Immunol*, 44[7]:1815-1817 (2007).

Paulie, S. et al., "Monoclonal Antibodies to Antigens Associated With Transitional Cell Carcinoma of the Human Urinary Bladder," *Cancer Immunol. Immunother*. 17: 173-179 (1984).

Penichet, M.L. and S.L. Morrison, "Antibody-Cytokine Fusion Proteins for the Therapy of Cancer," *J. Immunol. Methods* (248) 91-101 (2001).

Pierce Chemical Company catalog, technical section on cross-linkers, pp. 155-200, 1994 (2009 version provided, pp. 1-45).

Poljak, R.J. et al., "Production and structure of diabodies," *Structure*, 2:1121-1123 (1994).

Raghavan, M. and P.J. Bjorkman, "Fc Receptors and Their Interactions With Immunoglobulins," *Annu. Rev. Cell Dev. Biol.* (12) 181-220 (1996).

Ravetch, J.V. and S. Bolland, "IgG Fc Receptors," *Annu. Rev. Immunol.* (19) 275-290 (2001).

Reichert, J.M. et al., "Monoclonal antibody successes in the clinic," *Nature Biotechnology*, 23[9]: 1073-1078 (2005).

Richards, J.O. et al., "Optimization of antibody binding to Fc;RIIa enhances macrophage phagocytosis of tumor cells," *Mol Cancer Ther*, 7[8]:2517-2527 (2008).

Scallon, B.J. et al., "Higher levels of sialylated Fc gylcans in immunoglobulin G molecules can adversely impact functionality," *Mol Immunol*, 44[7]:1524-1534 (2007).

Shields, R.L. et al., "High Resolution Mapping of the Binding Site on Human IgG1 for FcyRI, FcyRIII and FcRn and Design of IgG1 Variants With Improved Binding to the FcyR," *J. Biol. Chem.* 276(9) 6591-6604 (2001).

Shields, R.L. et al.,"Lack of Fucose on Human IgG1 N-Linked Oligosaccharide Improves Binding to Human FcyRIII and Antibody-Dependent Cellular Toxicity," *J. Biol. Chem.* 277(30) 26733-26740 (2002).

Shinkawa, T. et al., "The Absence of Fucose But Not the Presence of Galactose or Bisecting *N*-Acetylglucosamine of Human IgG1 Complex-Type Oligosaccharides Shows the Critical Role of Enhancing Antibody-Dependent Cellular Cytotoxicity," *J. Biol. Chem.* 278(5) 3466-3473 (2003).

Sondermann, P. et al., "The 3.2-A Crystal Structure of the Human IgG1 Fc Fragment-FcyRIII Complex," *Nature* (406) 267-273 (2000).

Spiridon, C.I. et al., "Targeting Multiple Her-2 Epitopes With Monoclonal Antibodies Results in Improved Antigrowth Activity of a Human Breast Cancer Cell Line In vitro and In vivo," *Clin Cancer Res*. 8(6):1720-1730 (2002).

Strohl, W.R., "Optimization of Fc-mediated Effector Functions of Monoclonal Antibodies," *Curr. Opin. in Biotechnology*, 20:1-7 (2009).

Trail, P. and A.B. Bianchi, "Monoclonal Antibody Drug Conjugates in the Treatment of Cancer," *Curr. Opin. Immunol.* (11) 584-588 (1999).

Tsurushita, N. and M. Vasquez, "Humanization of Monoclonal Antibodies," *Elsevier Science USA*, 533-545 (2004).

Uchida, J. et al., "The Innate Mononuclear Phagocyte Network Depletes B Lymphocytes Through Fc Receptor-Dependent Mechanisms During Anti-CD20 Antibody Immunotherapy," *J. Exp. Med.* 199(12) 1659-1669 (2004).

Umana, P. et al., "Engineered Glycoforms of an Antineuro-Blastoma IgG1 With Optimized Antibody-Dependent Cellular Cytotoxicity Activity," *Nature* (17) 176-180 (1999).

Van Loghem, E., "Allotypic Markers," *Monogr. Allergy* 19:40-51 (1986).

Verhoeyen, M. et al., "Reshaping Human Antibodies: Grafting an Antilysozyme Activity," *Science*, 239:1534-1536 (1988).

Vetvicka, V. et al., "Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicitry of iC3b-Opsonized Target Cells," *J. Clin. Invest.* 98(1):50-61 (1996).

Vetvicka, V., et al., Targeting of Natural Killer Cells to Mammary Carcinoma via Naturally Occurring Tumor Cell-Bound iC3b and β-Glucan-Primed CR3 (CD11b/CD18), *J Immunol.* 159: 599-605 (1997).

Vugmeyster, Y., et al., "Depletion of B Cells by a Humanized Anti-CD20 Antibody PRO70769 in *Macaca fascicularis*," *J. Immunother.* 28(3):212-219 (2005).

Wang, S. et al., "NK-Cell Activation and Antibody-Dependent Cellular Cytotoxicity Induced by Rituximab-Coated Target Cells is Inhibited by the C3b Component of Complement," *Blood* 111(3): 1456-1463 (2008).

Wang, S. et al., "Depletion of the C3 Component of Complement Enhances the Ability of Rituximab-Coated Target Cells to Activate Human NK Cells and Improves the Efficacy of Monoclonal Antibody Therapy in an In Vivo Model," *Blood* 114:5322-5330 (2009).

Weng, W and R. Levy, "Expression of Complement Inhibitors CD45, CD55 and CD59 on Tumor Cells Does Not Predict Clinical Outcome After Rituximab Treatment in Follicular Non-Hodgkin Lymphoma," *Blood* 98:1352-1357 (2001).

WHO Review of the Notation for the Allotypic and Related Markers of Human Immunoglobulins, *J. Immunogen* (3) 357-362 (1976).

WHO Review of the Notation for the Allotypic and Related Markers of Human Immunoglobulins, *Eur. J. Immunol.* (6) 599-601 (1976).

Yan, J. et al., β-Glucan, A "Specific" Biologic Response Modifier That Uses Antibodies to Target Tumors for Cytotoxic Recognition by Leukocyte Complement Receptor Type 3 (CD11b/CD18), *J. Immunol.* 163: 3045-3052 (1999).

Yeung, Y.A. et al., "Engineering Human IgG1 Affinity to Human Neonatal Fc Receptor: Impact of Affinity Improvement on Pharmacokinetics in Primates," *J Immunol*, 182:7663-7671 (2010).

Zipfel, P.F. and C. Skerka, "Complement Regulators and Inhibitory Proteins," *Nat. Reviews Immunol.* 9(10):729-740 (2009).

FIGURE 4

| ID | Variant | CDC assay | | C1q SPR binding | |
|---|---|---|---|---|---|
| | | EC$_{50}$ (nM)[a] | Fold[b] | K$_d$ (nM)[c] | Fold[d] |
| - | Native IgG1[e] | 0.33 | 1 | 48 | 1 |
| - | S324T | 0.17 | 1.9 | 19 | 2.5 |
| - | H268F | 0.17 | 2.0 | 26 | 1.8 |
| - | S267E | 0.11 | 3.0 | 3.9 | 12 |
| FT | H268F/S324T | 0.098 | 3.3 | 4.6 | 11 |
| EF | S267E/H268F | 0.092 | 3.6 | 2.8 | 17 |
| ET | S267E/S324T | 0.061 | 5.4 | 1.2 | 41 |
| EFT | S267E/H268F/S324T | 0.048 | 6.9 | 1.0 | 47 |
| - | 113F | 0.089 | 3.7 | 6.9 | 7.1 |

[a]EC$_{50}$s were from four-parameter sigmoidal dose-response fits (n = 2).
[b]Fold = EC$_{50}$ (Native IgG1)/EC$_{50}$ (variant). [c]K$_d$ = K$_{d1}$/(1 + 1/K$_{d2}$) from a global two-state binding fit of SPR data. [d]Fold = K$_d$ (Native IgG1)/K$_d$ (variant).
[e]Antibodies had ocrelizumab variable regions.

FIGURE 7

| ID[a] | CDC | | ADCC | | ADCP | |
|---|---|---|---|---|---|---|
| | Potency[b] | Efficacy[c] | Potency[b] | Efficacy[c] | Potency[b] | Efficacy[c] |
| FT | 3.3 | 1.1 | 1.2 | 1.2 | 1.2 | 1.2 |
| EFT | 6.9 | 1.1 | 0.045 | 0.68 | 0.91 | 0.94 |
| FT + DE | 3.3 | 1.1 | 22 | 3.4 | 3.7 | 1.2 |
| FT + AE | 3.2 | 1.1 | 5.3 | 2.1 | 4.7 | 1.2 |
| EFT + AE | 23 | 1.1 | 1.2 | 1.0 | 0.46 | 1.0 |
| DE | 1.0 | 0.94 | 22 | 3.3 | 5.4 | 1.2 |
| AE | 1.2 | 1.0 | 8.3 | 2.5 | 2.5 | 1.3 |

[a]Variant ID's as in Table 1, plus: DE (S239D/I332E) and AE (G236A/I332E). [b]Potency Fold = $EC_{50}$ (Native IgG1)/$EC_{50}$ (variant). [c]Efficacy Fold = Maximum Lysis (variant)/Maximum Lysis (Native IgG1).

FIGURE 9

| | FcγRI | | FcγRIIa H131 | | FcγRIIa R131 | | FcγRIIb | | FcγRIIIa V158 | | FcγRIIIa F158 | |
|---|---|---|---|---|---|---|---|---|---|---|---|---|
| ID | $K_d$ (nM) | Fold | $K_d$ (μM) | Fold | $K_d$ (μM) | Fold | $K_d$ (μM) | Fold | $K_d$ (μM) | Fold | $K_d$ (μM) | Fold |
| IgG1 | 0.17 | 1 | 1.2 | 1 | 1.6 | 1 | 4.6 | 1 | 0.33 | 1 | 2.2 | 1 |
| FT | 0.25 | 0.70 | 0.80 | 1.5 | 2.4 | 0.67 | 12 | 0.38 | 0.33 | 1.0 | 2.2 | 1.0 |
| EFT | 0.11 | 1.6 | 0.35 | 3.5 | 0.045 | 37 | 0.25 | 18 | 1.0 | 0.32 | 11 | 0.21 |
| FT + DE | 0.021 | 8.2 | 0.21 | 5.8 | 0.18 | 9.2 | 0.47 | 9.9 | 0.0058 | 57 | 0.066 | 33 |
| FT + AE | 0.26 | 0.67 | 0.043 | 28 | 0.35 | 4.7 | 3.1 | 1.5 | 0.12 | 2.8 | 0.55 | 4.0 |
| EFT + AE | 0.10 | 1.8 | 0.035 | 35 | 0.0073 | 220 | 0.038 | 120 | 0.15 | 2.2 | 0.65 | 3.4 |

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: glycine-serine polymer linker

<400> SEQUENCE: 1
```

```
Gly Ser Gly Gly Ser
1               5

<210> SEQ ID NO 2
<211> LENGTH: 5
<212> TYPE: PRT
<213> ORGANISM: Artificial Sequence
<220> FEATURE:
<223> OTHER INFORMATION: glycine-serine polymer linker

<400> SEQUENCE: 2

Gly Gly Gly Gly Ser
1               5

<210> SEQ ID NO 3
<211> LENGTH: 4
<212> TYPE: PRT
<213> ORGANISM: Artificial Sequence
<220> FEATURE:
<223> OTHER INFORMATION: glycine-serine polymer linker

<400> SEQUENCE: 3

Gly Gly Gly Ser
1
```

ANTIBODY VARIANTS WITH ENHANCED COMPLEMENT ACTIVITY

RELATED APPLICATIONS

This application claims the benefit under 35 U.S.C. §119 (e) to U.S. Provisional Patent Application 61/296,316 filed Jan. 19, 2010, which is incorporated by reference in its entirety.

TECHNICAL FIELD

The present invention describes Fc variants with enhanced ability to recruit complement and mediate effector functions.

BACKGROUND OF THE INVENTION

Monoclonal antibodies (mAbs) are successful as therapeutics due in part to their ability to bring to bear the destructive capabilities of the immune system against specific target cells. In a variety of in vivo and in vitro settings, antibody coating of targets has been shown to mediate potent killing mechanisms such as complement-dependent cytotoxicity (CDC), antibody-dependent cellular cytotoxicity (ADCC), and antibody-dependent cellular phagocytosis (ADCP). All of these effector functions are mediated by the antibody Fc region.

The "classical" complement system is the antibody-dependent complement cascade, which consists of over twenty tightly-regulated proteins, C1 through C9. The trigger for classical complement activation is the initial binding to antibody-coated target by complement protein C1q, a bundle of six heterotrimeric subunits composed of globular heads and collagen-like tails.

The most widely recognized mechanism of complement-mediated target destruction is lysis by the membrane-attack complex (MAC), a transmembrane channel created by complexation of C5b, C6, C7, C8, and C9 proteins. This noncellular process, commonly referred to as CDC, is thought to be relevant to the clinical activity of some anti-tumor antibodies (Gelderman et al., 2004, Trends Immunol 25[3]:158-64). Less established for antibody drugs, although potentially no less relevant, are cellular-based complement mechanisms that are mediated by interaction between opsonic C3 and C4 components and complement receptors (CR1, CR3, and CR4) expressed on effector cells.

Optimization of complement activity appears as an unlikely means to increase therapuetic antibody efficacy. Take for example the therapuetic anti-CD20 antibody rituximab. Complement protein C3 has been shown to inhibit rituximab-mediated natural killer (NK) cell activation and ADCC (Wang et al., 2008, Blood 111[3]:1456-63), impacting antibody activity in vivo (Wang et al., 2009, Blood). Further, there is the observed absence of complement-mediated cytotoxicity in vitro using tumor cells from different response groups (Weng et al., 2001, Blood 98[5]:1352-7), and the uncompromised activity of other anti-CD20 mAbs in complement deficient mice (Hamaguchi et al., 2005, J Immunol 174[7]:4389-99; Uchida et al., 2004, J Exp Med 199[12]:1659-69). Thus, taken in whole these reports cast doubt on increasing the efficacy of therapuetic antibodies by altering complement activity.

In spite of this, the instant disclosure provides variant polypeptides, Fc, that alter complement activity. In the context of anti-CD20 antibodies, these Fc variants demonstrate increased efficacy relative to anti-CD20 antibodies without these Fc variants.

SUMMARY OF THE INVENTION

The present invention provides novel Fc variants that provide enhanced complement- and FcγR-mediated effector functions. In a preferred embodiment, the Fc variants of the invention are part of antibodies.

The Fc variants of the invention comprise two or more substitutions, wherein said substitutions improve binding to complement protein C1q or enhance CDC. In one embodiment, said variant Fc regions comprise two or more substitutions selected from the group consisting of 267E, 268F, and 324T; of particular use in the present invention, the variant Fc regions herein comprise a variant selected from the group consisting of 267E/268F, 267E/324T, 268F/324T, and 267E/268F/324T.

In additional embodiments of the invention, substitutions that enhance CDC are combined with substitutions that improve binding to one or more FcγRs and enhance ADCC and/or ADCP. In preferred embodiments, such combination variants comprise one or more CDC-enhancing substitutions selected from the group consisting of 267E, 268F, 268Y, 276R, and 324T, and further comprise one or more FcγR-enhancing substitutions selected from the group consisting of 236A, 239D, 239E, 332D, and 332E, wherein numbering is according to the EU index as in Kabat. In some embodiments, such combination variants comprise one or more CDC-enhancing substitutions selected from the group consisting of 267E, 268F, and 324T, and further comprise one or more FcγR-enhancing substitutions selected from the group consisting of 236A, 239D, and 332E.

The present invention provides isolated nucleic acids encoding the Fc variants described herein. The present invention provides vectors comprising said nucleic acids, optionally, operably linked to control sequences. The present invention provides host cells containing the vectors, and methods for producing and optionally recovering the Fc variants.

The novel Fc variants described herein may find use in a therapeutic product.

The present invention provides compositions comprising antibody variants described herein, and a physiologically or pharmaceutically acceptable carrier or diluent.

The present invention contemplates therapeutic and diagnostic uses for the Fc variants disclosed herein.

BRIEF DESCRIPTION OF THE DRAWINGS

FIG. 4. CDC activities and human C1q binding affinities of Fc variant antibodies.

FIG. 7. Summary of fold improvements for multiple cellular and non-cellular effector arms.

FIG. 9. Binding affinities of Fc variant antibodies for human Fcγ receptors measured by SPR.

DETAILED DESCRIPTION OF THE INVENTION

Figure 1:
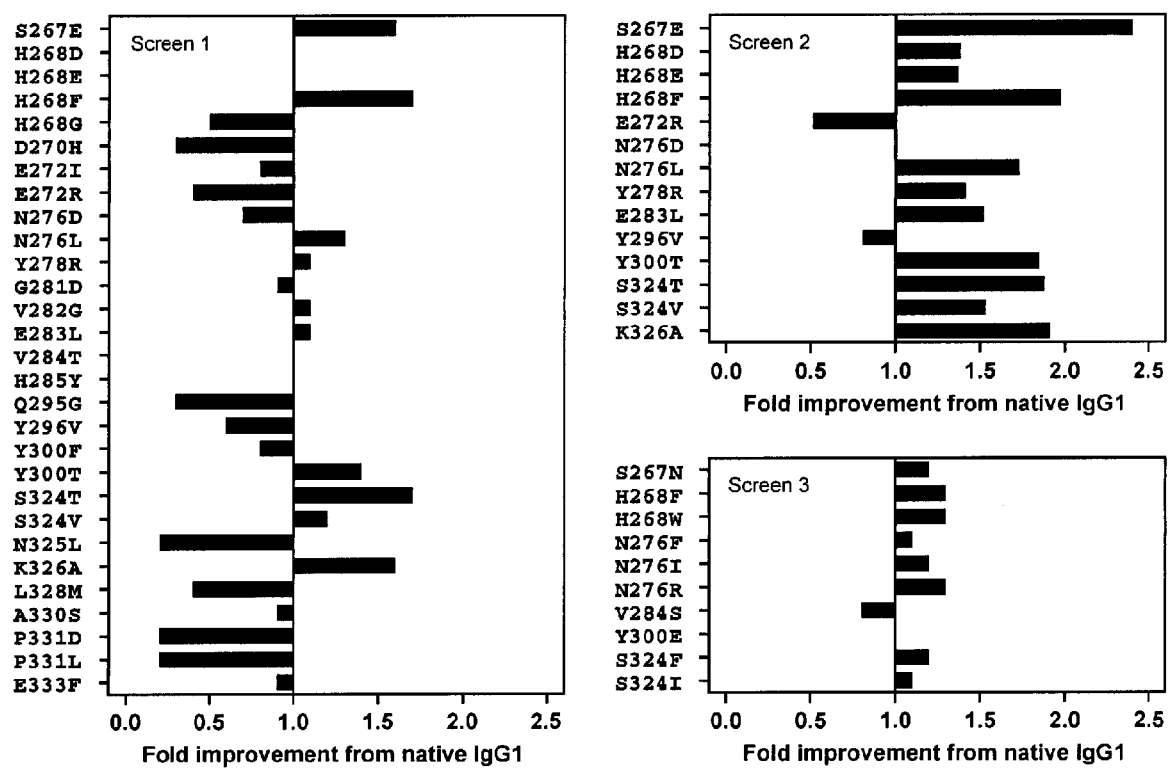
FIG. 1. Primary screens for CDC activity of Fc variant anti-CD20 mAbs against opsonized Raji cells using human complement. Screens 1 and 2 used 50,000 Raji cells as targets; Screen 3 used 40,000 Raji cells. Cell viability was measured by Alamar Blue®-based detection. Data were fit to a four-parameter sigmoidal dose-response curve using GraphPad Prism (La Jolla, Calif.). Fold improvements were calculated as Fold=$EC_{50}$ (Native IgG1)/$EC_{50}$ (variant).

The following patent applications are incorporated by reference in their entirety herein: U.S. Ser. No. 10/672,280, filed Sep. 26, 2003; U.S. Ser. No. 10/822,231, filed Mar. 26, 2004; U.S. Ser. No. 11/124,620, filed May 5, 2005; U.S. Ser. No. 11/174,287, filed Jun. 30, 2005; U.S. Ser. No. 11/396,495, filed Mar. 31, 2006; U.S. Ser. No. 11/538,406, filed Oct. 3, 2006; U.S. Ser. No. 11/538,411, filed Oct. 3, 2006; U.S. Ser. No. 12/020,443, filed Jau. 25, 2008; U.S. Ser. No. 11/274,065, filed Nov. 14, 2005; U.S. Ser. No. 11/436,266, filed May 17, 2006; U.S. Ser. No. 11/932,151, filed Oct. 31, 2007; and U.S. Ser. No. 12/341,769, filed Dec. 22, 2008.

FC

The ability to mediate cytotoxic and phagocytic effector functions are potent mechanisms by which antibodies destroy targeted cells. The Fc region links the recognition domain of antibodies to these effector functions through an interaction with Fc receptors and ligands. Manipulation of these effector functions by alteration of the Fc region has important implications in the treatment of numerous medical conditions, for example cancer, autoimmune diseases and infectious diseases.

To these ends, the instant disclosure provides altered Fc regions werein two or more amino acids within the Fc region are substituted. The positions of the Fc region and the amino acid substituted to are as follows: 267E, 267N, 268D, 268E, 268F, 268G, 268W, 268Y, 270H, 2721, 272R, 276D, 276F, 276I, 276L, 276R, 278R, 281D, 282G, 283L, 284S, 284T, 285Y, 295G, 296V, 300E, 300F, 300T, 324F, 324I, 324T, 324V, 325L, 326A, 328M, 330S, 331 D, 331 L, and 333F, wherein numbering is according to the EU index as in Kabat.

From among these positions, a variant Fc region with altered effector functions can be selected from two or more substitutions among the group 267E, 268F, 268Y, 276R, and 324T or among 267E, 268F, and 324T.

Also described are combinations of amino acid substitutions within the Fc region that alter effector functions werein two or more substitutions are made, these combinations are as follows: 267E/268Y/324T, 267E/268F/324T, 267E/268Y/276R, 267E/276R/324T, 267E/324T, 267E/268F/276R, 267E/268Y/300T, 267E/300T/324T, 268Y/300T, 324T, 268F/324T, 268Y/276R/300T, 276R/324F, 268F/300T/324T, 267E/268F/300T, 267E/276R, 267E/276R/300T, 268Y/324T, 268F/276R/300T, 268Y/300T, 268Y/276R/324T, 267E/268Y, 268F/276R/324T, 268Y/324V, 276F/300T, 276R/324V, 300T/324F, 300T/324T, 276R/300T/324T, 276R/324T, 268Y/324F, 276R/300T, 268Y/276R, 300T/324V, 268Y/276F, 268F/276R, 267E/300T, and 276F/324T, wherein numbering is according to the EU index as in Kabat. From among these combinations, a variant Fc region with altered effector functions can be: 267E/268F, 267E/324T, 268F/324T, 267E/268F/324T, 267E/268Y/324T, 267E/268Y/276R, 267E/276R/324T, and 267E/268F/276R or 267E/268F, 267E/324T, 268F/324T, and 267E/268F/324T.

Also described are combinations of amino acid substitutions within the Fc region that alter effector functions werein three or more substitutions are made, these combinations are as follows: 268F/324T/239D/332E, 268F/324T/236A/332E, 267E/268F/324T/239D/332E, 267E/268F/324T/236A/332E, 267E/268Y/324T/332E, 267E/268Y/324T/239D/332E, 267E/268Y/324T/236A/332E, 267E/332E, 267E/239D/332E, 267E/236A/332E, 267E/324T/332E, 267E/

324T/239D/332E, and 267E/324T/236A/332E, wherein numbering is according to the EU index as in Kabat. Among these combinations, a variant Fc region with altered effector function can be: 268F/324T/239D/332E, 268F/324T/236A/332E, 267E/268F/324T/239D/332E, 267E/268F/324T/236A/332E, 267E/324T/332E, 267E/324T/239D/332E, and 267E/324T/236A/332E.

The Fc region is found within heavy chain constant region of an antibody. By heavy chain constant region herein is meant the region of an antibody encoded by the mu, delta, gamma, alpha, or epsilon genes and define the antibody's isotype as IgM, IgD, IgG, IgA, and IgE, respectively, as further described below.

Amino acid positions within a heavy chain constant region can be designated using a sequential numbering system based on the first human immunoglobulin G1 (IgG1) sequenced, the EU antibody. Edelman et al. (1969). The most common reference for this convention is the Kabat sequence manual (Kabat et al., 1991). Using the EU system, the IgG constant region, as used herein, is from amino acid positions 118-447.

By "amino acid" herein is meant one of the 20 naturally occurring amino acids or any non-natural analogues that may be present at a specific, defined position. Amino acid encompasses both naturally occurring and synthetic amino acids. Although in most cases, when the protein is to be produced recombinantly, only naturally occurring amino acids are used.

Homophenylalanine, citrulline and norleucine are considered amino acids for the purposes of the invention. Amino acid also includes imino acid residues such as proline and hydroxyproline. The side chain may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

By "position" herein is meant a location in the sequence of a protein. Positions can be numbered sequentially, or according to an established format, for example the Kabat index for antibody variable regions or the EU index for antibody constant regions. For example, position 297 is a position in the human antibody IgG1, and the site of glycosylation. Corresponding positions are determined as outlined, generally through alignment with other wild-type sequences.

The present invention provides proteins comprising variant Fc regions. By "protein" herein is meant at least two covalently attached amino acids, which includes proteins, polypeptides, oligopeptides and peptides. The protein may be made up of naturally occurring amino acids and peptide bonds, or synthetic peptidomimetic structures, for example analogs such as peptoids. Again, when the protein is to be produced recombinantly, only naturally occurring amino acids are used.

By "variant" herein is meant a polypeptide sequence that differs from that of a wild-type sequence by virtue of at least one amino acid modification. Amino acid modifications can include substitutions, insertions and deletions, with the former being preferred in many cases. In general, variants can include any number of modifications, as long as the function of the protein is still present, as described below. However, in general, from 1, 2, 3, 4, 5, 6, 7, 8, 9 or 10 are generally utilized as often the goal is to alter function with a minimal number of modifications. In some cases, there are from 1 to 5 modifications, with from 1-2, 1-3 and 1-4 also finding use in many embodiments. It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 95% or up to 98 or 99% identity to the wild-type sequences or the parent sequences. It should be noted that depending on the size of the sequence, the percent identity will depend on the number of amino acids By "protein variant" or "variant protein" herein is meant a protein that differs from a wild-type protein by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% identity with a parent polypeptide sequence, and most preferably at least about 90% identity, more preferably at least about 95% identity.

By "parent polypeptide", "parent protein", "precursor polypeptide", or "precursor protein" as used herein is meant an unmodified polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant, and by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence.

An Fc variant comprises one or more amino acid modifications relative to a wild-type Fc polypeptide, wherein the amino acid modification(s) provide one or more optimized properties. An amino acid modification can be an amino acid substitution, insertion, or deletion in a polypeptide sequence, with multiple modifications being independently selected from these. By "amino acid substitution" or "substitution" herein is meant the replacement of an amino acid at a particular position in a parent polypeptide sequence with another amino acid. For example, the substitution S324T refers to a variant polypeptide, in this case a constant heavy chain variant, in which the serine at position 324 is replaced with threonine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

The Fc variants disclosed herein may have more than one amino acid modification as compared to the parent, for example from about one to fifty amino acid modifications, e.g., from about 1, 2, 3, 4, 5, 6, 7, 8, 9, or 10 amino acid modifications, from about one to about five amino acid modifications, etc. compared to the parent. The variant Fc variant sequences herein will possess about 80% identity with the parent Fc variant sequence, e.g., at least about 90% identity, at least about 95% identity, at least about 98% identity, at least about 99% identity, etc. Modifications disclosed herein also include glycoform modifications and other post-translational modifications as described below. Modifications may be made genetically using molecular biology, or may be made enzymatically or chemically.

Fc variants disclosed herein are defined according to the amino acid modifications that compose them. Thus, for example, the substitution S324T refers to a variant polypeptide, in this case a constant heavy chain variant, in which the serine at position 324 is replaced with threonine. Likewise, H268F/S324T defines an Fc variant with the substitution H268F and S324T relative to the parent Fc polypeptide, in this case the wild-type. Alternatively, the identity of the parent or WT amino acid may be unspecified, in which case the aforementioned variant is referred to as 268F/324T. It is noted that the order in which substitutions are provided is arbitrary, that is to say that, for example, 268F/324T is the same Fc variant as 324T/268F. Unless otherwise noted, constant region and Fc positions discussed herein are numbered according to the EU index or EU numbering scheme (Kabat et al., 1991, Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, hereby entirely incorporated by reference).

By "Fc" or "Fc region" herein is meant the polypeptide comprising the constant region of an antibody excluding the first constant region immunoglobulin domain. The IgA, IgD, and IgG heavy chains are composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively, while IgE and IgM are composed of five immunoglobulin domains VH-CH1-CH2-CH3-CH4 (heavy chain variable domain, heavy chain constant domain 1, heavy chain constant domain 2, heavy chain constant domain 3, and heavy chain constant domain 4). The Fc can include the flexible hinge N-terminal to these domains. Thus, Fc refers to the last two constant domains of IgA, IgD, and IgG and the last three constant domains of IgE and IgM.

For IgA and IgM, Fc may include the J chain.

In certain embodiments, the Fc variants disclosed herein are based on human IgG sequences, and thus human IgG sequences are used as the "base" sequences against which other sequences are compared, including but not limited to sequences from other organisms, for example rodent and primate sequences.

By "IgG" herein is meant a polypeptide belonging to the class of antibodies that are substantially encoded by the immunoglobulin gamma gene. In humans this class comprises IgG1, IgG2, IgG3, and IgG4. In mice this class comprises IgG1, IgG2a, IgG2b, and IgG3.

It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs.

By "residue" herein is meant a position in a protein and its associated amino acid identity. For example, Asparagine 297 (also referred to as Asn297, also referred to as N297) is a residue in the human antibody IgG1.

In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first antibody are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm, after alignment.

In another embodiment, equivalent residues are within about 0.1 nm after alignment.

Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant.

Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

The human IgG heavy chain Fc region is usually defined to comprise residues C226 or P230 to its carboxyl-terminus, wherein the numbering is according to the EU index as in Kabat.

By "immunoglobulin (Ig) domain" herein is meant a region of an immunoglobulin that exists as a distinct structural entity as ascertained by one skilled in the art. Ig domains typically have a characteristic β-sandwich folding topology.

The Fc region of an antibody interacts with a number of Fc receptors and ligands, imparting an array of important functional capabilities. By "Fc receptor" or "Fc ligand" as used herein is meant a protein molecule from any organism that binds to the Fc region to form an Fc-ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs.

For the IgG class the Fc gamma receptors (FcγRs) are an important family of Fc receptors.

FcγRs typically have an extracellular domain that mediates binding to Fc, a membrane spanning region, and an intracellular domain that may mediate some signaling event within the cell. These receptors mediate communication between antibodies and the cellular arm of the immune system (Raghavan et al., 1996, Annu Rev Cell Dev Biol 12:181-220; Ravetch et al., 2001, Annu Rev Immunol 19:275-290, both hereby entirely incorporated by reference).

In humans, the FcγR family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, hereby entirely incorporated by reference).

These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells.

Formation of the Fc/FcγR complex recruits effector cells to sites of bound antigen, typically resulting in signaling events within the cells and important subsequent immune responses such as release of inflammation mediators, B cell activation, endocytosis, phagocytosis, and cytotoxic attack.

The different IgG subclasses have different affinities for the FcγRs, with IgG1 and IgG3 typically binding substantially better to the receptors than IgG2 and IgG4 (Jefferis et al., 2002, Immunol Lett 82:57-65, hereby entirely incorporated by reference). The FcγRs bind the IgG Fc region with different affinities. The extracellular domains of FcγRIIIa and FcγRIIIb are 96% identical, however FcγRIIIb does not have a intracellular signaling domain.

Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge.

The Fc variants disclosed herein can be optimized for improved or reduced binding to Fc receptors or Fc ligands. By "greater affinity" or "improved affinity" or "enhanced affinity" or "better affinity" than a wild-type Fc polypeptide, herein is meant that an Fc variant binds to an Fc receptor with a significantly higher equilibrium constant of association (KA or Ka) or lower equilibrium constant of dissociation (KD or Kd) than the wild-type Fc polypeptide when the amounts of variant and parent polypeptide in the binding assay are essentially the same.

For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to Biacore®, by one skilled in the art.

Accordingly, by "reduced affinity" as compared to a parent Fc polypeptide as used herein is meant that an Fc variant binds an Fc receptor with significantly lower KA or higher KD than the wild-type Fc polypeptide. Significantly higher includes an equilibrium constant 1.1, 1.2, 1.5, 2, 5, 10, 15, 20, 25, 50, 75, 100, 125, 150, 200 or more fold higher than the parent or wild-type Fc. Significantly lower includes an equilibrium constant 1%, 2%, 5%, 10%, 15%, 20%, 25%, 30%, 35%, 40%, 45%, 50%, 55%, 60%, 65%, 75%, 80%, 85%, 90%, 95%, 98% of that of the parent or wild-type Fc.

Greater or reduced affinity can also be defined relative to an absolute level of affinity.

As used herein, the cell-mediated reaction wherein non-specific cytotoxic cells that express FcγRs recognize bound antibody on a target cell and subsequently cause lysis of the target cell is antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290, both hereby entirely incorporated by reference).

The amino acid substitutions for altering ADCC are at one or more positions selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein the numbering of the residues in the Fc region is that of the EU index as in Kabat. Variants of this type are described in US Publication No. 2006/0024298, and in particular in FIG. 41, both of which are expressly incorporated by reference in its entirety.

As will be appreciated by those in the art, substitutions are independently selected and/or combined, in any combination, from this list and the lists below. Specific amino acid substitutions, again for use singly or in combination, are independently selected from the group consisting of D221K, D221Y, K222E, K222Y, T223E, T223K, H224E, H224Y, T225E, T225K, T225W, P227E, P227G, P227K, P227Y, P228E, P228G, P228K, P228Y, P230A, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234K, L234M, L234N, L234P, L234Q, L234R, L234S, L234T, L234V, L234W, L234Y, L235A, L235D, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236K, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P238Y, S239D, S239E, S239F, S239G, S239H, S239I, S239K, S239L, S239M, S239N, S239P, S239Q, S239R, S239T, S239V, S239W, S239Y, V240A, V240I, V240M, V240T, F241D, F241E, F241L, F241R, F241S, F241W, F241Y, F243E, F243H, F243L, F243Q, F243R, F243W, F243Y, P244H, P245A, K246D, K246E, K246H, K246Y, P247G, P247V, D249H, D249Q, D249Y, R255E, R255Y, E258H, E258S, E258Y, T260D, T260E, T260H, T260Y, V262A, V262E, V262F, V262I, V262T, V263A, V263I, V263M, V263T, V264A, V264D, V264E, V264F, V264G, V264H, V264I, V264K, V264L, V264M, V264N, V264P, V264Q, V264R, V264S, V264T, V264W, V264Y, D265F, D265G, D265H, D265I, D265K, D265L, D265M, D265N, D265P, D265Q, D265R, D265S, D265T, D265V, D265W, D265Y, V266A, V266I, V266M, V266T, S267D, S267E, S267F, S267H, S267I, S267K, S267L, S267M, S267N, S267P, S267Q, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, D280G, D280K, D280L, D280P, D280W, G281D, G281E, G281K, G281N, G281P, G281Q, G281Y, V282E, V282G, V282K, V282P, V282Y, E283G, E283H, E283K, E283L, E283P, E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296D, Y296E, Y296G, Y296H, Y296I, Y296K, Y296L, Y296M, Y296N, Y296Q, Y296R, Y296S, Y296T, Y296V, N297D, N297E, N297F, N297G, N297H, N297I, N297K, N297L, N297M, N297P, N297Q, N297R, N297S, N297T, N297V, N297W, N297Y, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328E, L328F, L328G, L328H, L328I, L328K, L328M, L328N, L328P, L328Q, L328R, L328S, L328T, L328V, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330M, A330N, A330P, A330R, A330S, A330T, A330V, A330W, A330Y, P331D, P331F, P331H, P331I, P331L, P331M, P331Q, P331R, P331T, P331V, P331W, P331Y, I332A, I332D, I332E, I332F, I332H, I332K, I332L, I332M, I332N, I332P, I332Q, I332R, I332S, I332V, I332W, I332Y, E333F, E333H, E333I, E333L, E333M, E333P, E333T, E333Y, K334F, K334I, K334L, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat.

Of particular interest are those ADCC variants that increase binding to FcγRIIIa, including, but not limited to, 236A, 236S, 239D, 239E, 332D, 332D, 268D, 268E (the latter two being chosen only if the 268F substitution is not part of the increased CDC modifications), 243L, 330Y, and 330L, alone or in any combination, including any combination with the CDC substitutions described herein.

As used herein, the cell-mediated reaction wherein non-specific cytotoxic cells that express FcγRs recognize bound antibody on a target cell and subsequently cause phagocytosis of the target cell as antibody dependent cell-mediated phagocytosis (ADCP).

As used herein, complement dependent cytotoxicity (CDC) is the reaction wherein one or more complement protein components recognize bound antibody on a target cell and subsequently cause lysis of the target cell.

In some embodiments, the Fc variants improve FcRn binding. Such variants can enhance the in vivo pharmacokinetic properties of the antibodies. Variants that increase binding to FcRn and/or improve pharmacokinetic properties include but are not limited to substitutions at positions 259, 308, 428, and 434, including but not limited to for example 259I, 308F, 428L, 428M, 434S, 434H, 434F, 434Y, 434M, and 428L/434S (U.S. Ser. No. 12/341,769, filed Dec. 22, 2008, U.S. Ser. No. 11/274,065, filed Nov. 14, 2005; U.S. Ser. No. 11/436, 266, filed May 17, 2006; U.S. Ser. No. 11/932,151, filed Oct. 31, 2007; and U.S. Ser. No. 12/341,769, filed Dec. 22, 2008, all of which are incorporated by reference in their entirety). Other variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9):6591-6604, entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524, entirely incorporated by reference). Other modifications for modulating FcRn binding are described in Yeung et al., 2010, J Immunol, 182:7663-7671.

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, both hereby entirely incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins.

Fc Fusion

The present invention provides for an "Fc fusion". By Fc fusion herein is meant a protein wherein one or more polypeptides is operably linked to Fc. Fc fusion is herein meant to be synonymous with the terms "immunoadhesin", "Ig fusion", "Ig chimera", and "receptor globulin" as used in the art (Huang, 2009, Curr Opin Biotechnology 20:692-699; Chamow et al., 1996, Trends Biotechnol 14:52-60; Ashkenazi et al., 1997, Curr Opin Immunol 9:195-200, both hereby entirely incorporated by reference).

An Fc fusion combines the Fc region of an immunoglobulin with a fusion partner, which in general may be any protein, polypeptide or small molecule. The role of the non-Fc part of an Fc fusion, the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, e.g., an extracellular receptor that is implicated in disease.

Fusion partners may be linked to any region of an Fc region, including at the N- or C-termini, or at some residue in-between the termini. In one embodiment, a fusion partner is linked at the N- or C-terminus of the Fc region.

The term "linker" or "linker sequence" or "spacer" or "tethering sequence" is used to denote polypeptides comprising two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). A variety of linkers may find use in some embodiments described herein to covalently link Fc regions to a fusion partner.

Homo-or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis.

The linker peptide may predominantly include the following amino acid residues: Gly, Ser, Ala, or Thr.

The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used. Useful linkers include glycine-serine polymers, including for example (GS)n, (GSGGS)n [SEQ ID NO: 1], (GGGGS)n [SEQ ID NO: 2], and (GGGS)n [SEQ ID NO: 3], where n is an integer of at least one, glycine-alanine polymers, alanine-serine polymers, and other flexible linkers.

Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

Other linker sequences may include any sequence of any length of CL/CH1 domain but not all residues of CL/CH1 domain; for example the first 5-12 amino acid residues of the CL/CH1 domains. Linkers can be derived from antibody light chain, for example Cκ or Cλ. Linkers can be derived from antibody heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g. TCR, FcR, KIR), hinge region-derived sequences, and other natural sequences from other proteins.

Antibodies

The present invention provides an antibody comprising a variant Fc region. By antibody herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (υ), delta (δ), gamma (γ), epsilon (ε), and alpha (α) which encode the IgM, IgD, IgG (IgG1, IgG2, IgG3, and IgG4), IgE, and IgA (IgA1 and IgA2) isotypes respectively.

By "isotype" or "immunoglobulin isotype" herein is meant any subclas of immunoglobulins defined by the chemical and antigenic characteristics of their constant regions. Human immunoglobulin isotypes are IgG1, IgG2, IgG3, IgG4, IgA1, IgA2, IgM1, IgM2, IgD, and IgE. In the context of IgG antibodies, the IgG isotypes each have three CH regions. The distinguishing features between these antibody classes are their constant regions, although subtler differences may exists in the variable region.

Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Antibody herein is meant to include full length antibodies and antibody fragments, and can refer to a natural antibody from any organism, an engineered antibody, or an antibody generated recombinantly for experimental, therapeutic, or other purposes.

Antibodies can have a number of structural forms, including but not limited to full length antibodies, antibody fragments, individual immunoglobulin domains. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

The quaternary structure of wild-type antibodies is that of a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains.

The light chain is composed of two immunoglobulin domains linked from N- to C-terminus in he order $V_L$-$C_L$, referring to the light chain variable domain and the light chain constant domain respectively. By "light chain constant region" or "constant light chain" or "CL" is meant the region of an antibody encoded by the kappa ($C_\kappa$) or lambda ($C_\lambda$) light chains. The constant light chain typically comprises a single domain, and as defined herein refers to positions 108-214 of $C_\kappa$ or $C_\lambda$, wherein the numbering is according to the EU index.

Each of the light and heavy chains are made up of two distinct regions referred to as the variable and constant regions.

The variable region contains the antigen binding determinants of the antibody, and thus determines the specificity of an antibody for its target antigen. By "variable region" or "Fv region" herein is meant the region of an antibody that comprises one or more Ig domains substantially encoded by any of the $V_\kappa$ or $V_\lambda$, and/or VH genes that make up kappa, lambda, and heavy chain immunoglobulin genetic loci respectively.

The variable region is so named because it is the most distinct in sequence from other antibodies within the same class. The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant.

There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, entirely incorporated by reference, and the conserved features of antibodies are disclosed, for example, in Maynard et al., 2000, Annu Rev Biomed Eng 2:339-376, entirely incorporated by reference. In one embodiment, the antibody comprises an antibody fragment.

Specific antibody fragments include, but are not limited to (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

Antibodies described herein can incorporate Fc modifications in the context of any IgG isotype or IgG isotype Fc region, including but not limited to human IgG1, IgG2, IgG3, and/or IgG4. The IgG isotype may be selected such as to alter FcγR- and/or complement-mediated effector function(s). Hybrid IgG isotypes may also be useful. For example, U.S. Ser. No. 11/256,060 describes a number of hybrid IgG1/IgG2 constant regions that may find use in the particular invention. In some embodiments of the invention, antibodies may comprise means for isotypic modifications, that is, modifications in a parent IgG to the amino acid type in an alternate IgG. For example, an IgG1/IgG3 hybrid variant may be constructed by a substitutional means for substituting IgG1 positions in the CH2 and/or CH3 region with the amino acids from IgG3 at positions where the two isotypes differ. Thus a hybrid variant IgG antibody may be constructed that comprises one or more substitutional means, e.g., 274Q, 276K, 300F, 339T, 356E, 358M, 384S, 392N, 397M, 422I, 435R, and 436F. In other embodiments of the invention, an IgG1/IgG2 hybrid variant may be constructed by a substitutional means for substituting IgG2 positions in the CH2 and/or CH3 region with amino acids from IgG1 at positions where the two isotypes differ. Thus a hybrid variant IgG antibody may be constructed that comprises one or more substitutional means, e.g., one or more of the following amino acid substations: 233E, 234L, 235L, -236G (referring to an insertion of a glycine at position 236), and 327A.

Antibody polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem Immunol. 65:88-110; Gorman & Clark, 1990, Semin Immunol 2(6):457-66, both hereby entirely incorporated by reference).

Allelic forms of human antibodies have been well-characterized (WHO Review of the notation for the allotypic and related markers of human antibodies. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby entirely incorporated by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. The antibodies disclosed herein may be substantially encoded by any allotype, isoallotype, or haplotype of any immunoglobulin gene.

Another important region of the heavy chain is the hinge region. By "hinge" or "hinge region" or "antibody hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230 to 236.

Glycoform Modifications

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region.

By "Fab" herein is meant an antibody fragment that includes the first constant domain from heavy chain and the constant domain from the light chain together with the variable regions from both the heavy and light chains.

IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide normally consists of GlcNAc2Man3GlcNAc, with differing numbers of outer residues.

The carbohydrate moieties of antibodies disclosed herein will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of antibodies disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at residue 297.

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)2 typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the α1,4 mannose of the mature core carbohydrate structure. The bisecting GlcNAc can be enzymatically attached to the mature core carbohydrate structure by a α(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

Described herein are antibodies that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In one embodiment, the antibodies disclosed herein are modified to control the level of fucosylated and/or bisecting oligosaccharides that are covalently attached to the Fc region.

A variety of methods are well known in the art for generating modified glycoforms (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Ser. No. 12/434,533; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyl-transerase] and/or β1-4-N-acetylglucosaminyltransferase III [GnTIII]), by modifying carbohydrate(s) after the IgG has been expressed, or by expressing antibody in the presence of fucose analogs as enzymatic inhibitors. Other methods for modifying glycoforms of the antibodies disclosed herein include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). The use of a particular method to generate a modified glycoform is not meant to constrain embodiments to that method. Rather, embodiments disclosed herein encompass antibodies with modified glycoforms irrespective of how they are produced.

In one embodiment, antibodies disclosed herein are glycoengineered to alter the level of sialylation. Higher levels of sialylated Fc glycans in antibody G molecules can adversely impact functionality (Scallon et al., 2007, Mol Immunol. 44(7):1524-34), and differences in levels of Fc sialylation can result in modified anti-inflammatory activity (Kaneko et al., 2006, Science 313:670-673). Because antibodies may acquire anti-inflammatory properties upon sialylation of Fc core polysaccharide, it may be advantageous to glycoengineer the antibodies disclosed herein for greater or reduced Fc sialic acid content.

Engineered glycoform typically refers to the different carbohydrate or oligosaccharide; thus for example an immuoglobulin may comprise an engineered glycoform. Alternatively, engineered glycoform may refer to the antibody that comprises the different carbohydrate or oligosaccharide. In one embodiment, a composition disclosed herein comprises a glycosylated antibody having an Fc region, wherein about 51-100% of the glycosylated antibody, e.g., 80-100%, 90-100%, 95-100%, etc. of the antibody in the composition comprises a mature core carbohydrate structure which lacks fucose. In another embodiment, the antibody in the composition both comprises a mature core carbohydrate structure that lacks fucose and additionally comprises at least one amino acid modification in the Fc region. In an alternative embodiment, a composition comprises a glycosylated antibody having an Fc region, wherein about 51-100% of the glycosylated antibody, 80-100%, or 90-100%, of the antibody in the composition comprises a mature core carbohydrate structure which lacks sialic acid. In another embodiment, the antibody in the composition both comprises a mature core carbohydrate structure that lacks sialic acid and additionally comprises at least one amino acid modification in the Fc region. In yet another embodiment, a composition comprises a glycosylated antibody having an Fc region, wherein about 51-100% of the glycosylated antibody, 80-100%, or 90-100%, of the antibody in the composition comprises a mature core carbohydrate structure which contains sialic acid. In another embodiment, the antibody in the composition both comprises a mature core carbohydrate structure that contains sialic acid and additionally comprises at least one amino acid modification in the Fc region. In another embodiment, the combination of engineered glycoform and amino acid modification provides optimal Fc receptor binding properties to the antibody.

Other Modifications

Antibodies disclosed herein may comprise one or more modifications that provide optimized properties. Said modifications may be amino acid modifications, or may be modifications that are made enzymatically or chemically. Such modification(s) likely provide some improvement in the antibody, for example an enhancement in its stability, solubility, function, or clinical use. Disclosed herein are a variety of improvements that may be made by coupling the antibodies disclosed herein with additional modifications.

In one embodiment, the variable region of an antibody disclosed herein may be affinity matured, that is to say that amino acid modifications have been made in the VH and/or VL domains to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Antibodies disclosed herein may comprise one or more modifications that provide reduced or enhanced internalization of an antibody.

In one embodiment, modifications are made to improve biophysical properties of the antibodies disclosed herein, including but not limited to stability, solubility, and oligomeric state. Modifications can include, for example, substitutions that provide more favorable intramolecular interactions in the antibody such as to provide greater stability, or substitution of exposed nonpolar amino acids with polar amino acids for higher solubility. Other modifications to the antibodies disclosed herein include those that enable the specific formation or homodimeric or homomultimeric molecules. Such modifications include but are not limited to engineered disulfides, as well as chemical modifications or aggregation methods.

In further embodiments, the antibodies disclosed herein comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains, acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The antibodies disclosed herein may comprise modifications that include the use of unnatural amino acids incorporated using, including but not limited to methods described in Liu & Schultz, 2010, Annu Rev Biochem 79:413-444, herein expressly incorporated by reference. In some embodiments, these modifications enable manipulation of various functional, biophysical, immunological, or manufacturing properties discussed above. In additional embodiments, these modifications enable additional chemical modification for other purposes.

Other modifications are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the antibodies. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-TIS sequences into the antibodies disclosed herein.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody disclosed herein.

Covalent modifications are included within the scope of antibodies disclosed herein, and are generally, but not always, done post-translationally. For example, several types of covalent modifications can be introduced into the molecule by reacting specific amino acid residues with an organic derivatizing agent that is capable of reacting with selected side chains or the N- or C-terminal residues. In some embodiments, the covalent modification of the immunogloublins disclosed herein comprises the addition of one or more labels. The term "labeling group" means any detectable label. In some embodiments, the labeling group is coupled to the antibody via spacer arms of various lengths to reduce potential steric hindrance. Various methods for labeling proteins are known in the art and may be used in generating antibodies disclosed herein.

Nonhuman, Chimeric, Humanized, and Fully Human Antibodies

Antibodies disclosed herein may be substantially encoded by genes from any organism, e.g., mammals (including, but not limited to humans, rodents (including but not limited to mice and rats), lagomorpha (including but not limited to rabbits and hares), camelidae (including but not limited to camels, llamas, and dromedaries), and non-human primates, including but not limited to Prosimians, Platyrrhini (New World monkeys), Cercopithecoidea (Old World monkeys), and Hominoidea including the Gibbons and Lesser and Great Apes.

In the most preferred embodiments, the antibodies disclosed herein may be substantially human. The variable region of an antibody can compose sequences from a variety of species. In some embodiments, the antibody variable region can be from a nonhuman source, including but not limited to mice, rats, rabbits, camels, llamas, and monkeys. In some embodiments, the scaffold components can be a mixture from different species. As such, an antibody disclosed herein may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse or other nonhuman species and the constant region(s) from a human.

"Humanized antibodies" generally refer to non-human antibodies that have had the variable-domain framework regions swapped for sequences found in human antibodies. Generally in a humanized antibody the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (U.S. Pat. No. 5,693,762, incorporated entirely by reference.

The humanized antibody optimally also will comprise at least a portion of an antibody constant region, typically that of a human antibody, and thus will typically comprise a human Fc region. A variety of techniques and methods for humanizing, reshaping, and resurfacing non-human antibodies are well known in the art (See Tsurushita & Vasquez, 2004, Humanization of Monoclonal Antibodies, Molecular Biology of B Cells, 533-545, Elsevier Science (USA), and references cited therein, herein expressly incorporated by reference). In certain variations, the immunogenicity of the antibody is reduced using a method described in Lazar et al., 2007, Mol Immunol 44:1986-1998 and U.S. Ser. No. 11/004,590, entitled "Methods of Generating Variant Proteins with Increased Host String Content and Compositions Thereof", filed on Dec. 3, 2004, incorporated entirely by reference.

In one embodiment, the antibody is a fully human antibody with at least one modification as outlined herein. "Fully human antibody " or "complete human antibody" refers to a human antibody having the gene sequence of an antibody derived from a human chromosome with the modifications outlined herein. Fully human antibodies may be obtained, for example, using transgenic mice (Lonberg, 2008, Handb Exp Pharmacol 181:69-97) or human antibody libraries coupled with selection methods (Mondon et al., 2008, Front Biosci 13:1117-29; Lonberg, 2008, Curr Opin Immunol. 20[4]:450-9).

Target Antigens

The antibodies of the invention may target virtually any antigen. By "antigen" or "target" or "target antigen" herein is meant the molecule that is specifically bound by the variable region of an antibody or by the fusion protein or Fc fusion. An antigen can be a protein, a carbohydrate, a lipid, or other chemical.

Antigens that may be targeted by the disclosed molecules herein including but are not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, Al Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCK, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD3OL, CD32, CD33 (p67 proteins), CD34, CD38, CD40, CD4OL, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-1 (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF- 1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3,-4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (FLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF1OB (TRAIL R2 DRS, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (0X40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc- TRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (0X40 Ligand gp34, TXGP1), TNFSFS (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

Targets involved in oncological diseases that the disclosed molecules may bind include, but are not limited to those selected from the group consisting of: CD52, CD20, CD19, CD3, CD4, CD8, BMP6, IL12A, IL1A, IL1B, 1L2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, 1L2, INHA, TGFA, TGFB1, TGFB2, TGFB3, VEGF, CDK2, FGF10, FGF18, FGF2, FGF4, FGF7, IGF1R, IL2, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFB1I1, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NR0B1, NR0B2, NR1D2, NR1H2, NR1H4, NR112, NR2C1, NR2C2, NR2E1, NR2E3, NR2F1, NR2F2, NR3C1, NR3C2, NR4A1, NR4A2, NR5A1, NR5A2, NR6 μl, PGR, RARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, 1L2, IL24, INHA, INSL3, INSL4, KLK10, KLK12, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH2O, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYC1, DAB21P, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33 μl, SLC43 p1, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB 1, VEGF, VEGFC, ANGPTL3, BAI1, COL4A3, IL8, LAMA5, NRP1, NRP2, STAB 1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL1A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p161NK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MKI67 (Ki-67), NGFB (GF), NGFR, NME1 (M23A), PGR, PLAU (uPA), PTEN, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase Iia), TP53, AZGP1 (zinc-a-glycoprotein), BPAG1 (plectin), CDKN1A (p21Wap1/Cip1), CLDN7 (claudin-7), CLU (clusterin), ERBB2 (Her-2), FGF1, FLRT1 (fibronectin), GABRP (GABAa), GNAS1, 1D2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-III), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94), RON, c-Met, CD64, DLL4, PLGF, CTLA4, phophatidylserine, ROBO4, CD80, CD22, CD40, CD23, CD28, CD80, CD55, CD38, CD70, CD74, CD30, CD138, CD56, CD33, CD2, CD137, DR4, DRS, RANKL, VEGFR2, PDGFR, VEGFR1, MTSP1, MSP, EPHB2, EPHA1, EPHA2, EpCAM, PGE2, NKG2D, LPA, SIP, APRIL, BCMA, MAPG, FLT3, PDGFR alpha, PDGFR beta, ROR1, PSMA, PSCA, SCD1, and CD59.

Monoclonal antibody therapy has become an important therapeutic modality for treating autoimmune and inflammatory disorders (Chan & Carter, 2010, Nature Reviews Immunology 10:301-316; Reichert et al., 2005, Nature Biotechnology 23[9]:1073-1078; herein expressly incorporated by reference). Many proteins have been implicated in general autoimmune and inflammatory responses, and thus may be targeted by the immungloublins of the invention. Autoimmune and inflammatory targets include but are not limited to C5, CCL1 (1-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (1-TAC/IP-9), CXCL12 (SDF1), CXCL13, CXCL14, CXCL2, CXCL3, CXCL5 (ENA-78/ LIX), CXCL6 (GCP-2), CXCL9, 1L13, 1L8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, MO, 1L13, Il17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8R8, IL9, IL9R, IL10, IL10RA, IL10RB, IL11, IL12RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1I1, TGFB2, TGFB3, TGFB1, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, and RNF110 (ZNF144).

The molecules described herein may have specifity for one or more targets involved in asthma selected from the group consisting of CSF1 (MCSF), CSF2 (GM-CSF), CSF3 (GCSF), FGF2, IFNA1, IFNB1, IFNG, histamine and histamine receptors, IL1A, IL1B, IL2, IL3, IL4, IL5, IL6, IL7, IL8, IL9, IL10, IL11, IL12A, IL12B, IL13, IL14, IL15, IL16, IL17, IL18, IL19, KITLG, PDGFB, IL2RA, IL4R, IL5RA, IL8RA, IL8RB, IL12RB1, IL12RB2, IL13RA1, IL13RA2, IL18R1, TSLP, CCLi, CCL2, CCL3, CCL4, CCL5, CCL7, CCL8, CCL13, CCL17, CCL18, CCL19, CCL20, CCL22, CCL24,CX3CL1, CXCL1, CXCL2, CXCL3, XCLi, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNF, TNFSF6,YY1, CYSLTR1, FCER1A, FCER2, LTB4R, B4R2, LTBR, and Chitinase.

Antigens that may be targeted in order to treat systemic lupus erythematosus (SLE) include but are not limited to CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGSI, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, IL11, IL4, INHA, INHBA, KLF6, TNFRSF7, CD28, CD38, CD69, CD80, CD83, CD86, DPP4, FCER2, IL2RA, TNFRSF8, TNFSF7, CD24, CD37, CD40, CD72, CD74, CD79A, CD79B, CR2, ILIR2, ITGA2, ITGA3, MS4A1, ST6GALI, CDIC, CHSTIO, HLA-A, HLA-DRA, and NT5E.; CTLA4, B7.1, B7.2, BIyS, BAFF, C5, IL-4, IL-6, IL-10, IFN-α, and TNF-α.

The molecules described herein may target antigens for the treatment of multiple sclerosis (MS), inlcuding but not limited to IL-12, TWEAK, IL-23, CXCL13, CD40, CD4OL, IL-18, VEGF, VLA-4, TNF, CD45RB, CD200, IFNgamma, GM-CSF, FGF, C5, CD52, and CCR2. An embodiment includes co-egagement of anti-IL-12 and TWEAK for the treatment of MS.

One aspect of the invention pertains to molecules capable of binding one or more targets involved in sepsis, in an embodiment two targets, selected from the group consisting TNF, IL-1, MIF, IL-6, IL-8, IL-18, IL-12, IL-23, FasL, LPS, Toll-like receptors, TLR-4, tissue factor, MIP-2, ADORA2A, CASP1, CASP4, IL-10, IL-1B, NFκB1, PROC, TNFRSFIA, CSF3, CCR3, ILIRN, MIF, NFκB1, PTAFR, TLR2, TLR4, GPR44, HMOX1, midkine, IRAK1, NFκB2, SERPINA1, SERPINE1, and TREM1.

In some cases, the molecules described herein may be directed against antigens for the treatment of infectious diseases. Infectious disease targets may be any antigen expressed on any pathogenic organism, including but not limited to bacteria, fungi, protozoa, parasites, and the like. Target antigens may be expressed on viruses including but not limited to adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, rabies virus, respiratory syncytial virus (RSV), rinderpest, rhinovirus, rotavirus, rubella, SARS virus, smallpox, viral meningitis, west nile virus, and the like. Target antigens may be expressed on bacteria including but not limited to *Bacillus antracis, Borrelia burgdorferi, Campylobacter jejuni, Chlamydia trachomatis, Clostridium botulinum, Clostridium tetani, Diptheria, E. coli, Enterococcus, Legionella, Helicobacter pylon, Mycobacterium rickettsia, Mycoplasma nesisseria, Pertussis, Pseudomonas aeruginosa, S. pneumonia, Streptococcus, Staphylococcus, Vibria cholerae, Yersinia pestis*, and the like. Infectious diseas target antigens may be expressed on fungi including but not limited to *Aspergillus fumigatus, Blastomyces dermatitidis, Candida albicans, Coccidioides immitis, Cryptococcus neoformans, Histoplasma capsulatum, Penicillium marneffei*, and the like. Target antigens may also be expressed on protozoa and parasites including but not limited to *chlamydia*, kokzidioa, *leishmania, malaria, rickettsia, trypanosome*, and the like. Infectious disease target antigens include but are not limited to Microbial Surface Component Recognizing Adhesive Matrix Molecules (MSCRAMMs), CIfA, CIfB, Cna, protein A, SdrG, SdrC, SdrD, SarE, Bbp, MAP, Type 5/8 *S. aureus* capsular polysaccharide, ABC transporter, lipoteichoic acid, Cp5, clumping factor A, PNAG, MAP10, *S. aureus* ABC transporter, *S. aureus* capsular polysaccharides, *S. aureus* clumping factor A, *S. aureus* lipoteichoic acid, *B. anthracis* protective antigen, *C. difficile* toxins A and B, Diarrheagenic *E. coli* Shiga toxins, rabies glycoprotein, influenza hemagglutinin HA, HIV gp120, HIV gp41, and RSV fusion (F) protein.

One skilled in the art will appreciate that any of the aforementioned target antigens, the ligands or receptors that bind them, or other members of their corresponding biochemical pathway, may be operably linked to the antibodies of the present invention in order to generate an Fc fusion. Thus for example, an Fc fusion that targets TNFa could be constructed by operably linking an Fc region to TNFR1 or TNFR2. Thus virtually any polypeptide, whether a ligand, receptor, or some other protein or protein domain, including but not limited to the aforementioned targets and the proteins that compose their corresponding biochemical pathways, may be operably linked to the antibodies of the present invention to develop an Fc fusion.

Conjugates

In one embodiment, the Fc molecules disclosed herein are "fusion proteins", sometimes referred to herein as "conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of conjugates and methods are described in Trail et al., 1999, Curr. Opin. Immunol. 11:584-588, incorporated entirely by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the antibody. Thus, for example, the conjugation of a toxin to an antibody targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment disclosed herein. Rather, these terms are used loosely to convey the broad concept that any antibody disclosed herein may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibody, or binding of a radionuclide to a chelating agent that has been covalently attached to the antibody. Additional embodiments utilize calicheamicin, auristatins, geldanamycin, maytansine, and duocarmycins and analogs. Antibody-drug conjugates are described in Alley et al., 2010, Curr Opin Chem Biol 14[4]:529-37, herein expreslly incorporated by reference.

In one embodiment, the Fc molecules disclosed herein are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, incorporated entirely by reference, cytokines may be fused to an antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12, IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In yet another embodiment, the Fc molecules disclosed herein may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent.

Production of Fc Molecules

Also disclosed herein are methods for producing and experimentally testing Fc molecules. The disclosed methods are not meant to constrain embodiments to any particular application or theory of operation. Rather, the provided methods are meant to illustrate generally that one or more antibodies may be produced and experimentally tested to obtain antibodies. General methods for antibody molecular biology, expression, purification, and screening are described in Antibody Engineering, edited by Kontermann & Dubel, Springer, Heidelberg, 2001; and Hayhurst & Georgiou, 2001, Curr Opin Chem Biol 5:683-689; Maynard & Georgiou, 2000, Annu Rev Biomed Eng 2:339-76;

In one embodiment disclosed herein, nucleic acids are created that encode the Fc molecules, and that may then be cloned into host cells, expressed and assayed, if desired. Thus, nucleic acids, and particularly DNA, may be made that encode each protein sequence. These practices are carried out using well-known procedures. For example, a variety of methods that may find use in generating antibodies disclosed herein are described in Molecular Cloning - A Laboratory Manual, 3rd Ed. (Maniatis, Cold Spring Harbor Laboratory Press, New York, 2001), and Current Protocols in Molecular Biology (John Wiley & Sons), both incorporated entirely by reference. There are a variety of techniques that may be used to efficiently generate DNA encoding antibodies disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode antibodies.

The Fc molecules disclosed herein may be produced by culturing a host cell transformed with nucleic acid, e.g., an expression vector, containing nucleic acid encoding the antibodies, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, yeast, and plant cells. For example, a variety of cell lines that may find use in generating antibodies disclosed herein are described in the ATCC® cell line catalog, available from the American Type Culture Collection.

In one embodiment, the Fc molecules are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternateembodiment, library proteins are expressed in bacterial cells. Bacterial expression systems are well known in the art, and include *Escherichia coli* (*E. coli*), *Bacillus subtilis, Streptococcus cremoris*, and *Streptococcus lividans*. In alternate embodiments, antibodies are produced in insect cells (e.g. Sf21/Sf9, *Trichoplusia ni* Bti-Tn5b1-4) or yeast cells (e.g. *S. cerevisiae, Pichia*, etc). In an alternate embodiment, antibodies are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the antibodies may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the Fc molecules disclosed herein may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating antibodies disclosed herein include but are not limited to those which enable protein expression in mammalian cells, bacteria, insect cells, yeast, and in in vitro systems. As is known in the art, a variety of expression vectors are available, commercially or otherwise, that may find use for expressing antibodies disclosed herein.

The disclosed Fc molecules can be encoded by multiple nucleic acid molecules. For example, the heavy and light chains of an antibody can be introduced into a host cell independently. Though present on separate nucleic acids, their expression yields a single polypeptide.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. Ni+2 affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an antibody may be purified using a His-tag by immobilizing it to a Ni+2 affinity column, and then after purification the same His-tag may be used to immobilize the antibody to a Ni+2 coated plate to perform an ELISA or other binding assay (as described below). A fusion partner may enable the use of a selection method to screen antibodies (see below). Fusion partners that enable a variety of selection methods are well-known in the art.

For example, by fusing the members of an antibody library to the gene III protein, phage display can be employed. Fusion partners may enable antibodies to be labeled. Alternatively, a fusion partner may bind to a specific sequence on the expression vector, enabling the fusion partner and associated antibody to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In one embodiment, antibodies are purified or isolated after expression. Proteins may be isolated or purified in a variety of ways known to those skilled in the art. Purification may be particularly useful in the invention for separating heterodimeric heavy chain species from homodimeric heavy chain species, as described herein. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, isoelectric focusing, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of antibodies disclosed herein. For example, the bacterial proteins A and G bind to the Fc region. Likewise, the bacterial protein L binds to the Fab region of some antibodies, as of course does the antibody's target antigen. Purification can often be enabled by a particular fusion partner. For example, antibodies may be purified using glutathione resin if a GST fusion is employed, Ni+2 affinity chromatography if a His-tag is employed, or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the screen or use of the antibodies. In some instances no purification is necessary. For example in one embodiment, if the antibodies are secreted, screening may take place directly from the media. As is well known in the art, some methods of selection do not involve purification of proteins.

In Vitro Experimentation

Antibodies may be screened using a variety of in vitro methods, including but not limited to those that use binding assays, cell-based assays, and selection technologies. Automation and high-throughput screening technologies may be utilized in the screening procedures. Screening may employ the use of a fusion partner or label. The use of fusion partners has been discussed above. By "labeled" herein is meant that the antibodies disclosed herein have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In one embodiment, the functional and/or biophysical properties of antibodies are screened in an in vitro assay. In vitro assays may allow a broad dynamic range for screening properties of interest. Particularly relevant for the present invention, the antibodies may be tested for their affinity for one or more antigens. Properties that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of antibodies to a protein or nonprotein molecule that is known or thought to bind the antibody. In one embodiment, the screen is a binding assay for measuring binding to the target antigen. In an alternate embodiment, the screen is an assay for binding of antibodies to an Fc ligand, including but are not limited to the family of FcγRs, the neonatal receptor FcRn, the complement protein C1q, and the bacterial proteins A and G. Said Fc ligands may be from any organism. In one embodiment, Fc ligands are from humans, mice, rats, rabbits, and/or monkeys. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the antibody. Assays may employ a variety of detection methods including but not limited to chromogenic, fluorescent, luminescent, or isotopic labels.

The biophysical properties of Fc molecules, for example stability and solubility, may be tested using a variety of methods known in the art. Protein stability may be determined by measuring the thermodynamic equilibrium between folded and unfolded states. For example, antibodies disclosed herein may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an antibody may be quantitatively or qualitatively determined using a wide range of methods that are known in the art. Methods which may find use for characterizing the biophysical properties of antibodies disclosed herein include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

In one embodiment, Fc molecules may be tested using one or more cell-based or in vitro assays. For such assays, antibodies, purified or unpurified, are typically added exogenously such that cells are exposed to antibodies described herein. These assays are typically, but not always, based on the biology of the ability of the antibody to bind to the target antigen and mediate some biochemical event, for example effector functions like cellular lysis, phagocytosis, ligand/receptor binding inhibition, inhibition of growth and/or proliferation, inhibition of calcium release and/or signaling, apoptosis and the like. Such assays often involve monitoring the response of cells to antibody, for example cell survival, cell death, cellular phagocytosis, cell lysis, change in cellular morphology, or transcriptional activation such as cellular expression of a natural gene or reporter gene. For example, such assays may measure the ability of antibodies to elicit cell killing, for example ADCC, ADCP, and CDC. Assays that measure cellular killing that is mediated by co-engagement of antigens are particularly relevant for the invention. For some assays additional cells or components, that is in addition to the target cells, may need to be added, for example serum complement, or effector cells such as peripheral blood monocytes (PBMCs), NK cells, macrophages, T cells, and the like. Such additional cells may be from any organism, e.g., humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In one embodiment, the DELFIA EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an antibody. Cell types for such assays may be prokaryotic or eukaryotic, and a variety of cell lines that are known in the art may be employed. Alternatively, cell-based screens are performed using cells that have been transformed or transfected with nucleic acids encoding the antibodies.

In Vivo Experimentation

The biological properties of the Fc moleculess disclosed herein may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the antibodies disclosed herein, a particular challenge arises when using animal models to evaluate the potential for in-human efficacy of candidate polypeptides— this is due, at least in part, to the fact that antibodies that have a specific effect on the affinity for a human Fc receptor may not have a similar affinity effect with the orthologous animal receptor. These problems can be further exacerbated by the inevitable ambiguities associated with correct assignment of true orthologues (Mechetina et al., 2002, Immunogenetics 54:463-468, incorporated entirely by reference), and the fact that some orthologues simply do not exist in the animal. Therapeutics are often tested in mice, including but not limited to nude mice, Rag-deficient mice, SCID mice, xenograft mice, and transgenic mice (including knockins and knockouts). For example, an antibody of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the drug to reduce or inhibit cancer growth and metastasis. Therapeutic antibodies herein can be tested in mouse strains NZB, NOD, BXSB, MRL/lpr, K/BxN and transgenics (including knockins and knockouts). Such mice can develop various autoimmune conditions that resemble human organ specific, systemic autoimmune or inflammatory disease pathologies such as systemic lupus erythematosus (SLE) and rheumatoid arthritis (RA). For example, an antibody disclosed herein intended for autoimmune diseases may be tested in such mouse models by treating the mice to determine the ability of the antibody to reduce or inhibit the development of the disease pathology. Because of the incompatibility between the mouse and human Fcγ receptor system, an alternative approach is to use a murine SCID model in which immune deficient mice are engrafted with human PBLs or PBMCs (huPBL-SCID, huPBMC-SCID) providing a semi-functional human immune system with human effector cells and Fc receptors. Other organisms, e.g., mammals, may also be used for testing. For example, because of their genetic similarity to humans, monkeys can be suitable therapeutic models, and thus may be used to test the efficacy, toxicity, pharmacokinetics, or other property of the antibodies disclosed herein. Tests of the antibodies disclosed herein in humans are ultimately required for approval as drugs, and thus of course these experiments are contemplated. Thus the antibodies disclosed herein may be tested in humans to determine their therapeutic efficacy, toxicity, pharmacokinetics, and/or other clinical properties.

In some embodiments, the Fc molecuels disclosed herein may be assessed for efficacy in clinically relevant animal models of various human diseases. In many cases, relevant models include various transgenic animals for specific antigens and receptors.

In one embodiment, the testing of the Fc molecules may include study of efficacy in primates (e.g. cynomolgus monkey model) to facilitate the evaluation of depletion of specific target cells harboring the target antigen. Additional primate models include but are not limited to use of the rhesus monkey to assess antibodies in therapeutic studies of autoimmune, transplantation and cancer.

Toxicity studies are performed to determine drug related-effects that cannot be evaluated in standard pharmacology profiles, or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated, are evaluated for cross-reactivity with normal tissues, immunogenicity/antibody production, conjugate or linker toxicity and "bystander" toxicity of radiolabelled species. Nonetheless, such studies may have to be individualized to address specific concerns and following the guidance set by ICH S6

(Safety studies for biotechnological products, also noted above). As such, the general principles are that the products are sufficiently well characterized, impurities/contaminants have been removed, that the test material is comparable throughout development, that GLP compliance is maintained.

The pharmacokinetics (PK) of the antibodies disclosed herein may be studied in a variety of animal systems, with the most relevant being non-human primates such as the cynomolgus and rhesus monkeys. Single or repeated i.v./s.c. administrations over a dose range of 6000-fold (0.05-300 mg/kg) can be evaluated for half-life (days to weeks) using plasma concentration and clearance. Volume of distribution at a steady state and level of systemic absorbance can also be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T1/2). Additional measured parameters could include compartmental analysis of concentration-time data obtained following i.v. administration and bioavailability.

Pharmacodynamic studies may include, but are not limited to, targeting specific cells or blocking signaling mechanisms, measuring inhibition of antigen-specific antibodies etc. The antibodies disclosed herein may target particular effector cell populations and thereby be direct drugs to induce certain activities to improve potency or to increase penetration into a particularly favorable physiological compartment. Such pharmacodynamic effects may be demonstrated in animal models or in humans.

Clinical Use

The Fc molecules disclosed herein may find use in a wide range of products. In one embodiment an antibody disclosed herein is a therapeutic, a diagnostic, or a research reagent. The antibodies may find use in a composition that is monoclonal or polyclonal. The antibodies disclosed herein may be used for therapeutic purposes. As will be appreciated by those in the art, the antibodies disclosed herein may be used for any therapeutic purpose that antibodies, Fc fusions, and the like may be used for. The antibodies may be administered to a patient to treat disorders including but not limited to cancer, infectious diseases, autoimmune and inflammatory diseases.

A "patient" for the purposes disclosed herein includes both humans and other animals, e.g., other mammals. Thus the antibodies disclosed herein have both human therapy and veterinary applications. The term "treatment" or "treating" as disclosed herein is meant to include therapeutic treatment, as well as prophylactic, or suppressive measures for a disease or disorder. Thus, for example, successful administration of an antibody prior to onset of the disease results in treatment of the disease. As another example, successful administration of an optimized antibody after clinical manifestation of the disease to combat the symptoms of the disease comprises treatment of the disease. "Treatment" and "treating" also encompasses administration of an optimized antibody after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an Fc molecule disclosed herein is administered to a patient having a disease involving inappropriate expression of a protein or other molecule. Within the scope disclosed herein this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the antibodies disclosed herein.

In preferred embodiments, the Fc molecules disclosed herein may be used to treat cancer. By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (eg. nasopharyngeal cancer, salivary gland carcinoma, and esophagael cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

In other preferred embodiments, the Fc molecules disclosed herein may be used to treat infectious diseases. By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, rabies virus, respiratory syncytial virus, rinderpest, rhinovirus, rotavirus, rubella, SARS virus, smallpox, viral meningitis, and the like. Infections diseases may also be caused by bacteria including *Bacillus antracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis, Pseudomonas aeruginosa, S. pneumonia, Streptococcus, Staphylococcus, Vibria cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as *Chlamydia*, kokzidioa, *leishmania, malaria, rickettsia, trypanosome*, and the like.

The Fc molecules disclosed herein may be used to treat autoimmune diseases. By "autoimmune diseases" herein include allogenic islet graft rejection, alopecia areata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

The Fc molecules disclosed herein may be used to treat inflammtory disorders. By "inflammatory disorders" herein include acute respiratory distress syndrome (ARDS), acute septic arthritis, adjuvant arthritis, juvenile idiopathic arthritis, allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

Some autoimmune and inflammatory diseases that may be targeted by the Fc moleucles disclosed herein include Systemic Lupus Erythematosus, Rheumatoid arthritis, Sjogren's syndrome, Multiple sclerosis, Idiopathic thrombocytopenic purpura (ITP), Graves disease, Inflammatory bowel disease, Psoriasis, Type I diabetes, and Asthma.

Furthermore, the Fc molecules disclosed herein may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological and neurodegenerative conditions such as Alzheimer's disease.

The variant Fc molecules described herein can be used in a method to reduce aberrant cells, the method comprisng administering to a subject in need an effective amount of the variant Fc molecule. An "effective amount" herein is meant the amount of a variant Fc molecule needed to amerliorate the symptoms of a condition or a condition present in subject. As used herein, "reduce" as in "reduce aberrant cells" means a lowering in the percentage of a particular cell type in vivo or in vitro. The particular cell type may be directly or indirectly bound by the variant Fc molecule and the particular cell type may be reduction relative to a control, such as untreated cells, by 5%, 10%, 15%, 20%, 25%, 30%, 35%, 40%, 45%, 50%, 55%, 60%, 65%, 70%, 80%, 85%, 90, 95% or more. By "aberrant cells" herein is meant cells whose activity or presence is deleterious, for example, tumor cells, autoimmune cells, or pathogen infected cells.

Formulation

Pharmaceutical compositions are contemplated wherein an antibody disclosed herein and one or more therapeutically active agents are formulated. Formulations of the antibodies disclosed herein are prepared for storage by mixing said antibody having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or antibodies; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In one embodiment, the pharmaceutical composition that comprises the antibody disclosed herein may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Some embodiments include at least one of the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration may be sterile. This is readily accomplished by filtration through sterile filtration membranes or other methods.

The Fc molecules disclosed herein may also be formulated as immunoliposomes. A liposome is a small vesicle comprising various types of lipids, phospholipids and/or surfactant that is useful for delivery of a therapeutic agent to a mammal. Liposomes containing the antibody are prepared by methods known in the art. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The Fc molecule and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated entirely by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and Pro-Lease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an Fc molecule disclosed herein, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the antibody may be directly applied as a solution or spray. As is known in the art, the pharmaceutical composition may be formulated accordingly depending upon the manner of introduction.

Subcutaneous administration may be used in circumstances where the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. Antibodies disclosed herein may be more amenable to subcutaneous administration due to, for example, increased potency, improved serum half-life, or enhanced solubility. As is known in the art, protein therapeutics are often delivered by IV infusion or bolus. The antibodies disclosed herein may also be delivered using such methods. For example, administration may be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Furthermore, antibodies disclosed herein may be amenable to oral delivery.

In addition, any of a number of delivery systems are known in the art and may be used to administer the antibodies disclosed herein. Examples include, but are not limited to, encapsulation in liposomes, microparticles, microspheres (e.g., PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol),polylactides, copolymers of L-glutamic acid and ethyl-L-gutamate, ethylene-vinyl acetate, lactic acid-glycolic acid copolymers such as the Lupron Depot®, and poly-D-(−)-3-hydroxybutyric acid. It is also possible to administer a nucleic acid encoding an antibody disclosed herein, for example by retroviral infection, direct injection, or coating with lipids, cell surface receptors, or other transfection agents. In all cases, controlled release systems may be used to release the antibody at or close to the desired location of action.

Dosing

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active antibody in the formulation may vary from about 0.1 to 100 weight %. In one embodiment, the concentration of the antibody is in the range of 0.003 to 1.0 molar. In order to treat a patient, a therapeutically effective dose of the antibody disclosed herein may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight. In one embodiment, dosages range from 1 to 10 mg/kg.

In some embodiments, only a single dose of the Fc molecule is used. In other embodiments, multiple doses of the antibody are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the antibodies disclosed herein are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the Fc molecules disclosed herein and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The Fc molecules disclosed herein may be administered concomitantly with one or more other therapeutic regimens or agents. The additional therapeutic regimes or agents may be used to improve the efficacy or safety of the antibody. Also, the additional therapeutic regimes or agents may be used to treat the same disease or a comorbidity rather than to alter the action of the antibody. For example, an antibody disclosed herein may be administered to the patient along with chemotherapy, radiation therapy, or both chemotherapy and radiation therapy.

The terms "in combination with" and "co-administration" are not limited to the administration of said prophylactic or therapeutic agents at exactly the same time. Instead, it is meant that the antibody disclosed herein and the other agent or agents are administered in a sequence and within a time interval such that they may act together to provide a benefit that is increased versus treatment with only either the antibody disclosed herein or the other agent or agents. In some embodiments, antibodies disclosed herein and the other agent or agents act additively, and sometimes synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

The Fc molecule disclosed herein may be administered in combination with one or more other prophylactic or therapeutic agents, including but not limited to cytotoxic agents, chemotherapeutic agents, antibiotics, antifungal agents, antiviral agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, other antibodies, Fc fusions, or antibodies, or other therapeutic agents. The therapies of the invention may be combined with other immunotherapies. The therapies of the invention may be combined with antagonists of chemokines or cytokines, including but not limited to antibodies and Fc fusions.

The the Fc molecule disclosed herein may be combined with other therapeutic regimens. For example, in one embodiment, the patient to be treated with an antibody disclosed herein may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Optionally, the radiation therapy may be administered as a single dose or as multiple, sequential doses. The skilled medical practitioner can determine empirically the appropriate dose or doses of radiation therapy useful herein. In accordance with another, an antibody disclosed herein and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient. It is of course contemplated that the antibodies disclosed herein may employ in combination with still other therapeutic techniques such as surgery.

EXAMPLES

Examples are provided below to illustrate the present invention. These examples are not meant to constrain the present invention to any particular application or theory of operation.

Example 1

Engineering of CDC-Enhanced anti-CD20 Antibodies

Single substitution variants for CDC activity were screened. Variant Fc domains including substitutions were constructed, expressed, and screened in the context of ocrelizumab (Vugmeyster et al., 2005, J Immunother 28[3]:212-9), a humanized anti-CD20 IgG1 antibody. The variable region VH and VL domains of ocrelizumab (also known as PRO70769 or rhuMAb 2H7) anti-human CD20 antibody were generated by gene synthesis (Blue Heron® Biotechnology, Bothell, Wash.) and subcloned into the vector pTT5 (National Research Council, Canada) (Durocher et al., 2002, Nucleic Acids Res 30[2]:E9) encoding human heavy IgG1 and light Cκ constant regions. Substitutions in the Fc domain were introduced using site-directed mutagenesis (QuikChange®, Stratagene, Cedar Creek, TX). Positions are numbered according to the EU index (Kabat et al., 1991). Heavy and light chain constructs were cotransfected into HEK293E cells (National Research Council, Canada) (Durocher et al., 2002, Nucleic Acids Res 30[2]:E9) for expression, and antibodies were purified using protein A affinity chromatography (GE Healthcare). Overall 38 single substitution variants were constructed and tested.

Variants were screened for CDC activity. Target Ramos or Raji cells were washed 2× in RHB Buffer (RPMI Medium 1640 containing 20 mM HEPES, 2 mM glutamine, 0.1% BSA, pH 7.2) by centrifugation and resuspension and seeded at 40,000 cells per well. Burkitt's lymphoma Ramos cell line was obtained from DSMZ (German Collection of Microorganisms and Cell Lines). Burkitt's lymphoma Raji cell line was obtained from American Type Culture Collection. Native IgG1 or variant antibody was added at the indicated final concentrations. Human serum complement (Quidel, San Diego, Calif.) was diluted with RHB buffer and added to opsonized target cells. Final complement concentration was one-eighteenth original stock. Plates were incubated for 2 hr at 37° C., Alamar Blue was added, cells were cultured overnight, and fluorescence was measured in relative fluorescence units. Data were normalized to maximal (Triton X-100) and minimal (complement alone) lysis and fit to a four-parameter sigmoidal dose-response curve using GraphPad Prism (La Jolla, Calif.).

Figure 2:
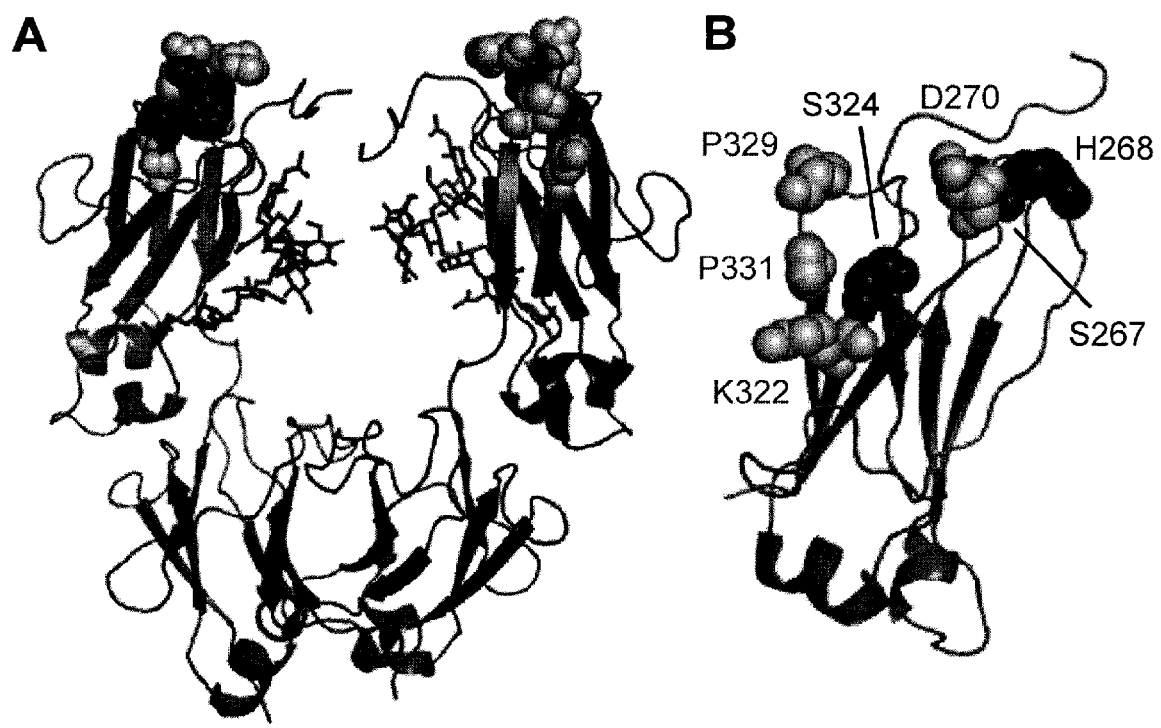
FIG. 2. Cartoon representation of human IgG1 antibody Fc from Protein Data Bank record 1E4K (Sondermann et al., 2000, Nature 406[6793]:267-73) with positions at which substitution modulates C1q binding affinity highlighted as space-filling spheres. The putative C1q binding center (D270, K322, P329, and P331) is colored light grey. Residues S267, H268, and S324 are indicated in dark grey. Oligosaccharides are represented as sticks. (A) Full Fc. (B) $C_H2$ domain only.

Fold improvements relative to native IgG1 ocrelizumab are plotted in FIG. 1. From these data, we identified three substitutions (S267E, H268F, S324T) in the human IgG1 $C_H2$ domain (FIG. 2) for further study. Single substitutions were combined in combination variants S267E/H268F (EF), S267E/S324T (ET), H268F/S324T (FT), S267E/H268F/S324T (EFT). Variants were constructed in the anti-CD20 context as described above. An IgG1/IgG3 chimera, referred to as 113F (Natsume et al., 2008, Cancer Res 68[10]:3863-72) was also constructed as a positive control for CDC enhancement. Antibodies were expressed and purified as described above.

Figure 3:
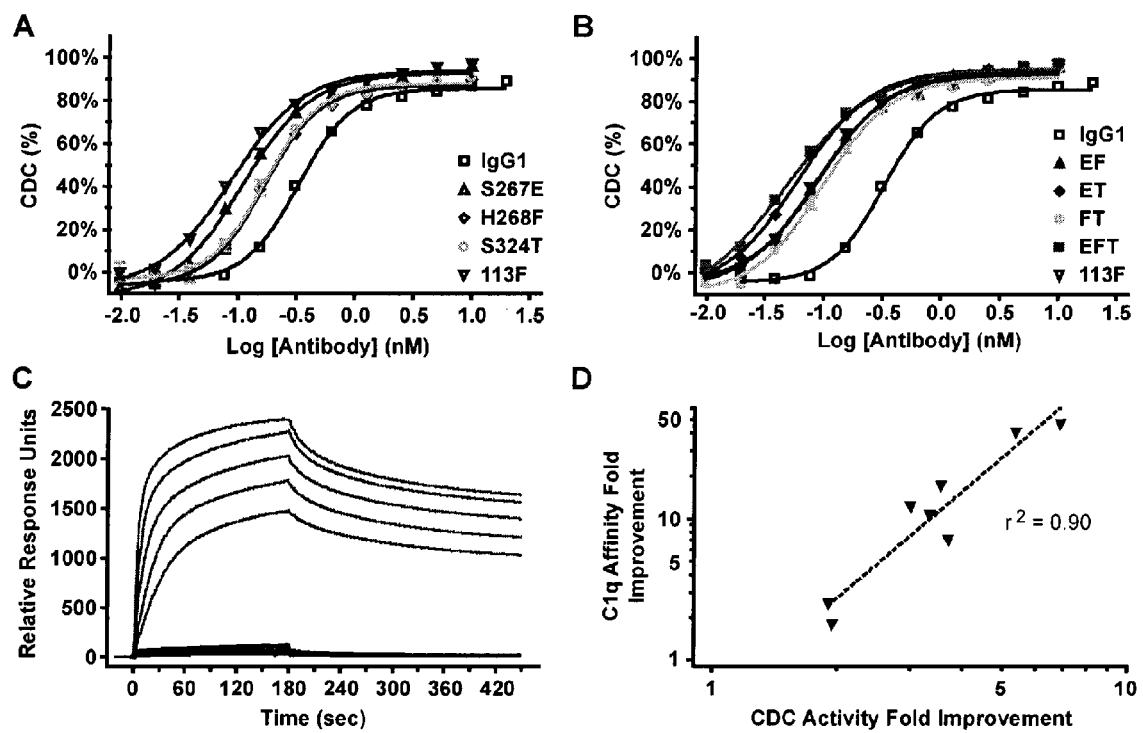
FIG. 3. Fc engineering generates variant anti-CD20 antibodies with enhanced binding affinity for C1q and enhanced cytotoxicity of CD20+ Ramos cells. (A-B) CDC activity of Fc variant anti-CD20 mAbs against opsonized Ramos cells using human complement. Antibody-dependent % lysis was measured at multiple antibody concentrations by Alamar Blue®-based detection (mean±SE of duplicate wells). EC$_{50}$s are listed in FIG. 4. (C) SPR sensorgrams for native IgG1 (lower set of five curves) and variant EFT (upper set of five curves) are shown. C1q concentrations range from 100 nM to 6.125 nM by 2-fold serial dilution. (D) Correlation between the fold improvements in C1q affinity as determined by SPR (FIG. 4) and CDC activity (FIGS. 3A,B and 4).

The relative CDC activity of the anti-CD20 Fc variants against Burkitt's lymphoma Ramos cells was examined (FIG. 3A-B). Human serum complement was added to opsonized target cells, cell viability was determined from Alamar Blue® fluorescence, and half-maximal effective concentration ($EC_{50}$) values of the antibody-dependent cell lysis were calculated (FIG. 4). The three single substitutions resulted in potency increases of 1.9- to 3.0-fold relative to native IgG1 ocrelizumab. When the single substitutions were combined, potencies further increased, ranging from 3.3-fold to 5.4-fold for double substitution variants and 6.9-fold for the triple. Several variants surpassed the potency of the 113F IgG1/IgG3 chimera (Natsume et al., 2008, Cancer Res 68[10]: 3863-72). Similar results were observed when targeting the Burkitt's lymphoma Raji cell line (data not shown).

The binding of the Fc variants to human C1q was measured using surface plasmon resonance (SPR). SPR measurements were performed in HBS-EP running buffer (10 mM HEPES pH 7.4, 0.15 M NaCl, 3 mM EDTA, 0.005% v/v surfactant P20, GE Healthcare) using a Biacore™ 3000 instrument (GE Healthcare). For determining C1q affinity, a protein A (Pierce Biotechnology) CM5 biosensor chip (GE Healthcare) was generated using a standard primary amine coupling protocol. The chip's reference channel was coupled to bovine serum albumin (BSA) to minimize nonspecific binding of C1q. Antibodies at 50 nM were immobilized on the protein A surface for 0.5 or 1 min at 10 pL/min. C1q (GenWay Biotech, San Diego, Calif.) in 2-fold serial dilutions (starting at 100 or 25 nM, 5 concentrations total) was injected over antibody-bound surface for 3 min at 30 pL/min followed by a 4.5 min dissociation phase. C1q molarity was calculated using the molecular weight of the C1q hexameric bundle, 410 kDa. Response units for C1q association and dissociation never dropped below the RU level of protein A-captured antibody for native IgG1 or any of the variants, suggesting that antibody was not displaced from the protein A chip upon binding to C1q and that protein A and C1q can be bound simultaneously. After each cycle, the surface was regenerated by injecting glycine buffer (10 mM, pH 1.5). In order to subtract nonspecific C1q binding to antibody-coated protein A surface, an Fc variant with greatly ablated CDC activity was included. Sensorgrams were processed by zeroing time and response before the injection of C1q and by subtracting appropriate nonspecific signals (response of BSA-blocked reference channel, response of an Fc variant with ablated CDC, and response of running buffer). Kinetic parameters were determined by global fitting of association and dissociation phase data with a two-state binding model (A+B⇌AB⇌AB*). $K_d$ was calculated as $K_{d1}/(1+1/K_{d2})$.

Sensorgrams (FIG. 3C) were fit with a two-state binding model (FIG. 4). Although the fitted $K_d$ values do not represent the actual $K_d$ between C1q globular head and Fc, they nonetheless reflect the relative affinity of the C1q multimeric bundle for an opsonized surface. The C1q affinities of the variants showed similar rank order to their CDC potencies, with a correlation coefficient of $r^2=0.90$ (P<0.0005) (FIG. 3D). Consistent with its 6.9-fold increase in CDC potency, the S267E/H268F/S324T (EFT) variant had the tightest C1q affinity as well, an increase of 47-fold over native IgG1 and 6.5-fold over the 113F positive control.

Figure 5:
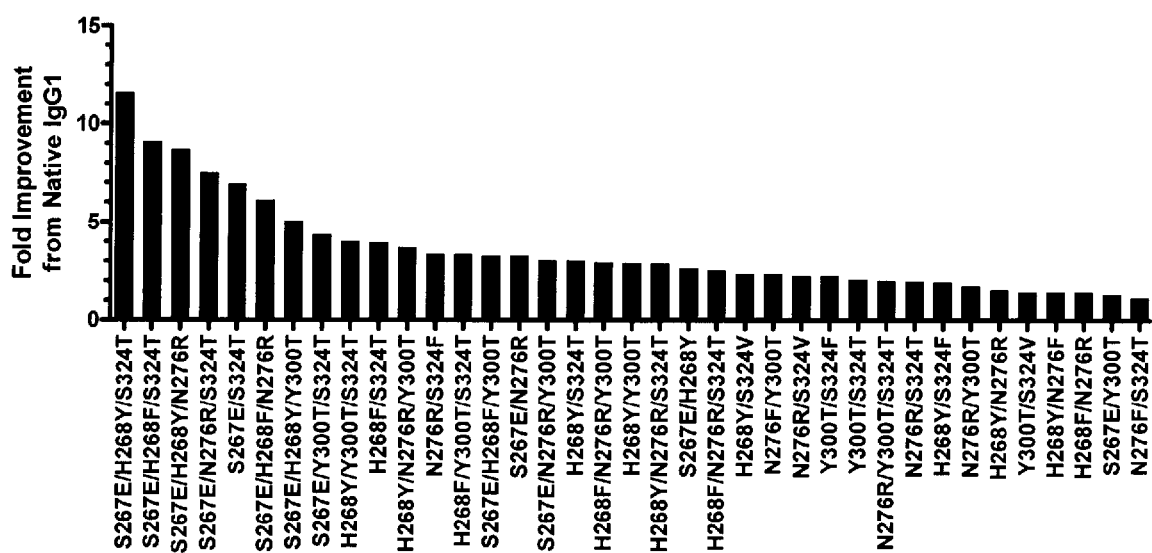
FIG. 5. CDC activity of additional Fc variant anti-CD20 mAbs against opsonized Ramos cells using human complement. Antibody-dependent % lysis was measured at multiple antibody concentrations by Alamar Blue®-based detection, and EC$_{50}$ fold improvement compared to native IgG1 was calculated.

Based on these data, additional substitution combinations were designed. Variants were constructed, expressed, and screened in the context of ocrelizumab as described above. We examined the relative CDC activity of these anti-CD20 Fc variants against Burkitt's lymphoma Ramos cells (FIG. 5).

Example 2

Engineering of Anti-CD20 Antibodies with Augmented CDC, ADCC, and ADCP Activity In order to develop variants with broadly enhanced effector function, CDC-enhancing substitutions were combined with variants previously characterized for improved FcγR-mediated activity (Lazar et al., 2006, Proc Natl Acad Sci U S A 103[11]:4005-10; Richards et al., 2008, Mol Cancer Ther 7[8]:2517-27). These include two double substitution variants, one with broad affinity enhancement to all FcγRs (239D/I332E, referred to here as DE), and the other with selective affinity enhancement to FcγRIIa and FcγRIIIa relative to FcγRIIb (G236A/I332E, referred to as AE). Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Substitutions were added via site-directed mutagenesis to H268F/S324T and S267E/H268F/S324T, resulting in a set of four variants, each with four or five substitutions. The EFT triple was chosen as the variant with the greatest CDC activity, while the FT double was of interest as the most potent CDC variant lacking S267E, which impaired FcγR-mediated effector function due to decreased FcγRIIIa and increased FcγRIIb affinity. For simplicity these variant combinations are referred to by adding the FcγR substitutions as a suffix to the CDC variants, i.e. FT+DE, FT+AE, EFT+DE, and EFT+AE.

Combination variants were constructed and expressed in the context of anti-CD20 IgG1 ocrelizumab as described above. To serve as an Fc isotype control, the variable region domains of the anti-respiratory syncytial virus (RSV) antibody motavizumab (Mejias et al., 2005, Antimicrob Agents Chemother 49[11]:4700-7) were generated by gene synthesis (Blue Heron® Biotechnology, Bothell, Wash.). Fc variant versions of the anti-RSV antibodies were constructed by subcloning into the appropriate IgG1 and Cκ pTT5 vectors from ocrelizumab Fc variants.

Figure 6:
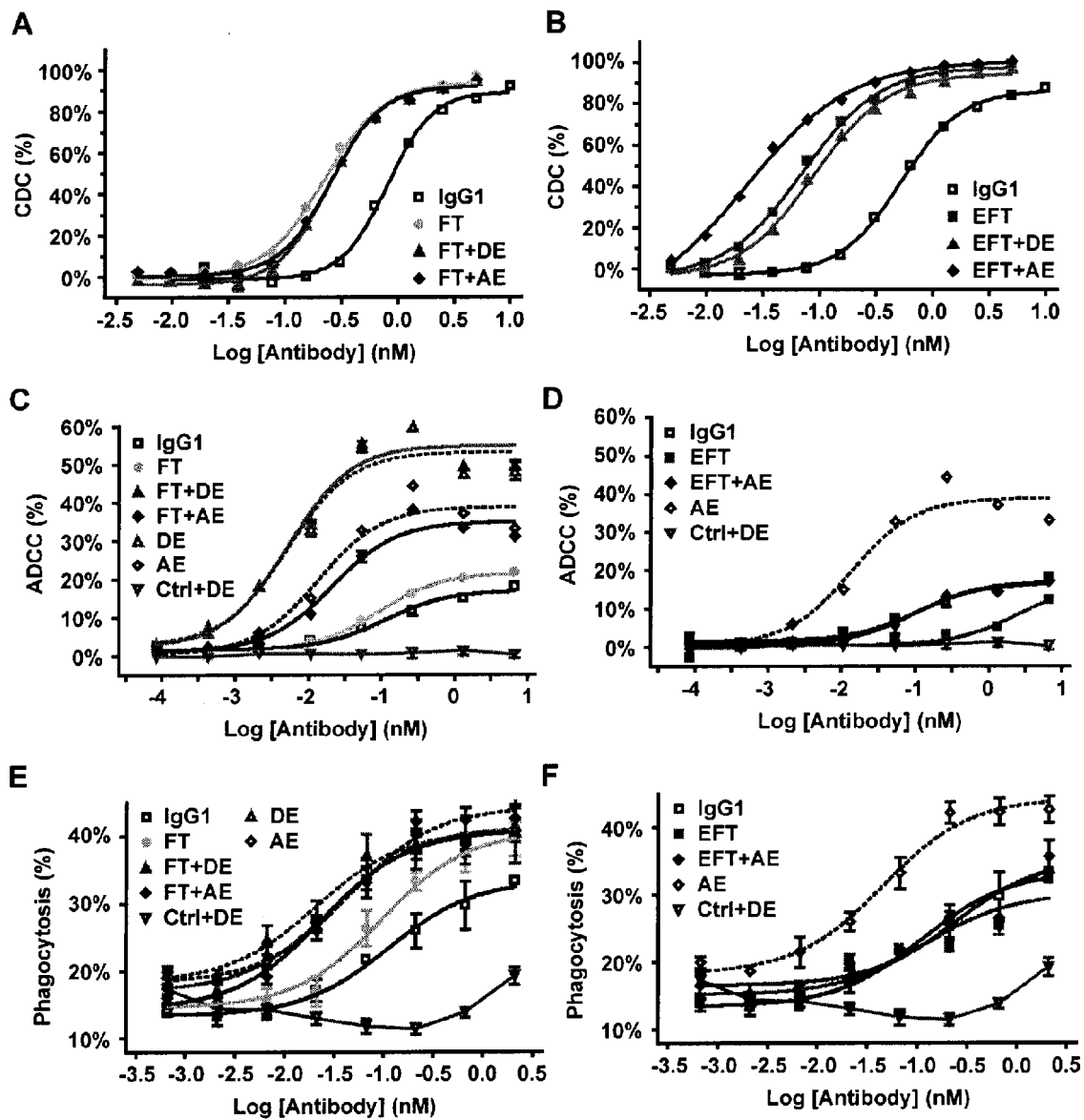
FIG. 6. Fc variants enhance CDC, ADCC, and ADCP. (A-B) CDC activity of Fc variant anti-CD20 mAbs against opsonized Ramos cells using human complement. Antibody-dependent % lysis was measured at multiple antibody concentrations by Alamar Blue-based detection (mean±SE of duplicate wells). (C-D) ADCC activity of Fc variant anti-CD20 mAbs against Ramos cells using human PBMCs (FcγRIIa genotype was H131/R131, FcγRIIIa genotype was V158/F158). Antibody-dependent % cytotoxicity was measured at multiple antibody concentrations by lactate dehydrogenase release (mean±SE of triplicate wells). (E-F) Phagocytosis activity of Fc variant anti-CD20 mAbs against Ramos cells using purified human monocyte-derived macrophages. Antibody-dependent % phagocytosis was measured at multiple antibody concentrations by flow cytometry (mean±SE of triplicate wells). Macrophages for this experiment were H131/R131 FcγRIIa and V158/F158 FcγRIIIa genotype. Ctrl+DE for ADCC (C-D) and ADCP (E-F) experiments represents an isotype control anti-RSV antibody with DE substitutions. For all of the data shown, fold improvements in EC$_{50}$ and maximal lysis relative to native IgG1 are listed in FIG. 7.

CDC assays of the combination variants confirmed that the enhanced potency conferred by the initial engineering remained upon adding the substitutions (FIG. 6A-B). These results were supported by correlated increases in C1q affinity (data not shown). Unexpectedly, it was found that the EFT+AE variant gained an additional 3.3-fold in CDC activity (and, similarly, C1q affinity, data not shown) relative to the EFT triple variant (FIG. 7). However, this synergy was not observed with the EFT+DE combination (FIG. 6B). Subsequent work identified I332E and S267E as the synergistic pair, but that their synergy was absent in the presence of 239D (data not shown). The five-substitution EFT+AE variant was the most potent complement mediator, providing enhancement to CDC $EC_{50}$ by 23-fold in the context of the anti-CD20 (FIG. 7).

Figure 8:
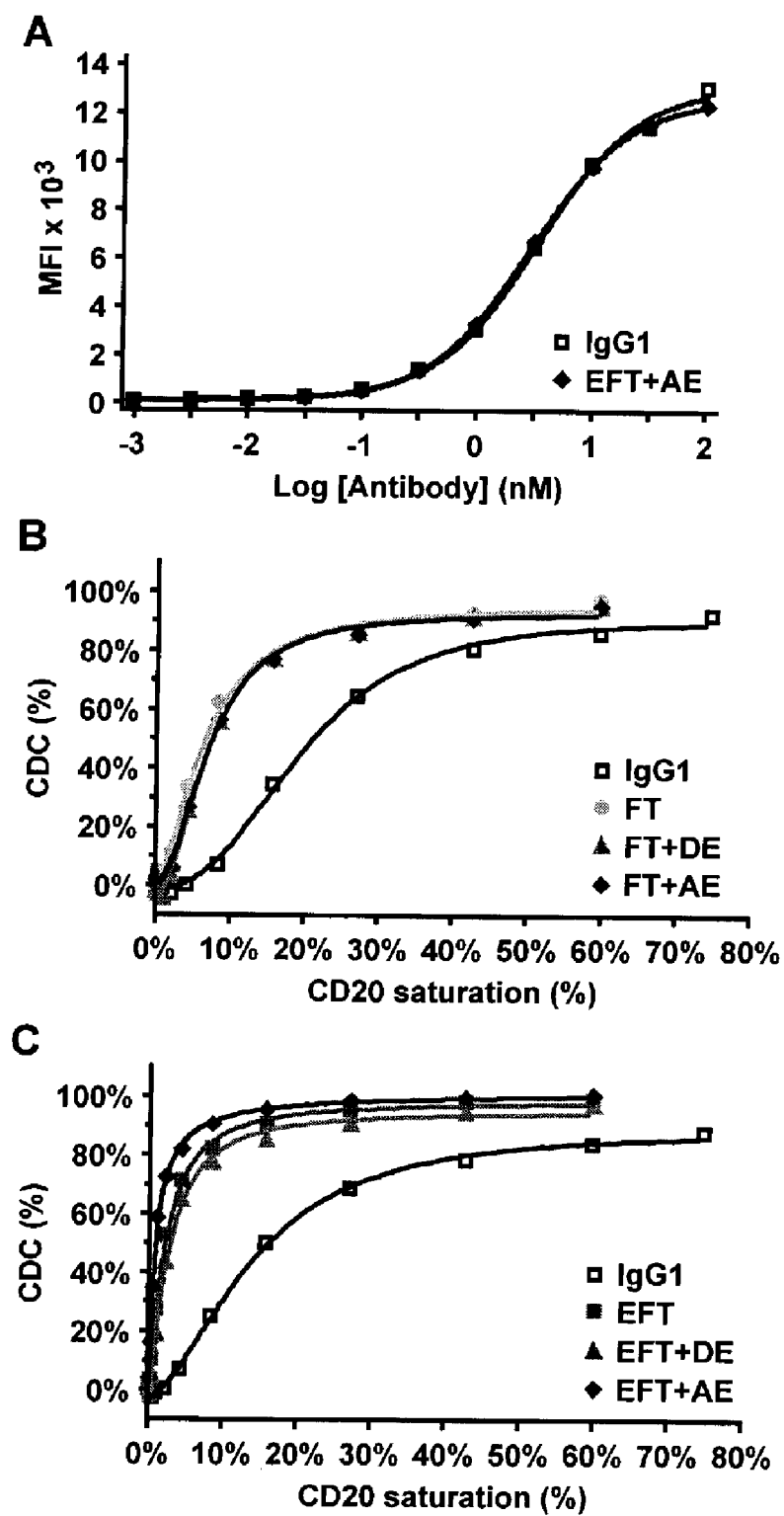
FIG. 8. Estimation of antigen saturation required for a given level of CDC activity based on cell-surface binding data. (A) A Ramos cell-surface binding assay was used to measure CD20 binding affinity of the indicted anti-CD20 antibodies. Antibodies were detected using fluorescently labeled secondary antibodies on a FACSCanto™ II flow cytometer. The fitted EC$_{50}$ of native IgG1 was 3.4 nM; the fitted EC$_{50}$ of variant EFT+AE was 2.9 nM. (B-C) Replotting of CDC activities from antibody concentration to % CD20 saturation. The CDC data from FIG. 6A-B were transformed using the native IgG1 binding data from panel A according to the following equation: % CD20 saturation=100%·(1/(1+[native IgG1 EC$_{50}$]/[Antibody])).

An experiment was carried out to characterize the dependence of the CDC activity of the variants on CD20 saturation level. Ramos cells were washed 2× in RHB Buffer (RPMI Medium 1640 containing 20 mM HEPES, 2 mM glutamine, 0.1% BSA, pH 7.2) by centrifugation and resuspension and seeded at 40,000 cells per well. Native IgG1 or variant antibody was added at the indicated final concentrations. Plates were incubated for 30 min at room temperature, and then washed 4× in PBS. Then, PE-labeled goat secondary anti-human IgG Fc antibodies (Jackson ImmunoResearch, West Grove, Pa.) were added and the mixture incubated for an additional 30 minutes on ice. Cells were washed in PBS twice, fixed with 1% paraformaldehyde, then analyzed on a FACSCanto II (BD Biosciences, San Jose, Calif.). Resulting mean fluorescent intensity (MFI) values were fit to a three-parameter sigmoidal dose-response curve using GraphPad Prism (La Jolla, Calif.). A transform of the data based on cell-surface binding indicated that the variants lowered the CD20 saturation level needed for CDC activity (FIG. 8); remarkably, the CDC $EC_{50}$ of the EFT+AE variant corresponded to less than 1% CD20 saturation level versus ~15% for native IgG1.

Affinities of the variant anti-CD20 antibodies to activating and inhibitory human FcγRs were examined by SPR. Human Fc gamma receptor protein FcγRI was obtained from R&D Systems (Minneapolis, MN). Human FcγRIIa, FcγRIIb, and FcγRIIIa receptor proteins were produced at Xencor. FcγRIIa, FcγRIIb, and FcγRIIIa genes were obtained from the Mammalian Gene Collection (American Type Culture Collection). The extracellular domains of these were subcloned into the vector pcDNA3.1Zeo (Invitrogen) with a C-terminal 6×His tag, transfected into HEK293T cells and purified using nickel affinity chromatography (Qiagen®, Valencia, Calif.). SPR measurements were performed in HBS-EP running buffer (10 mM HEPES pH 7.4, 0.15 M NaCl, 3 mM EDTA, 0.005% v/v surfactant P20, GE Healthcare) using a Biacore™ 3000 instrument (GE Healthcare). FcγR affinity was determined as described (Richards et al., 2008, Mol Cancer Ther 7[8]:2517-27), and the results reported are the average obtained from separate Langmuir fittings of the data from the two independent flow cells of the biosensor chip.

The results of the binding experiment are shown in FIG. 9. The FT double substitution marginally affected FcγR binding if at all, with the most significant perturbation being a slightly lower affinity for FcγRIIb. Addition of the DE and AE substitutions to this variant dramatically improved FcγR binding, resulting in variants with broad enhancement to FcγRs, particularly the isoforms of FcγRIIIa (FT+DE), or selective enhancement for FcγRIIa and FcγRIIIa relative to FcγRIIb (FT+AE). The EFT CDC-enhancing variant displayed reduced FcγRIIIa affinity and sharply increased binding to FcγRIIa R131 and FcγRIIb. Combination with the AE substitutions produced a variant (EFT+AE) with substantially higher FcγRIIa affinity, a greater H131 FcγRIIa:FcγRIIb ratio yet high FcγRIIb affinity, and FcγRIIIa binding slightly better than native IgG1.

To examine the effect of these FcγR binding profiles on effector recruitment, the anti-CD20 variant antibodies were studied in cell-based ADCC and ADCP assays. These experiments used the Ramos cell line as target cells, and either purified peripheral blood mononuclear cells (PBMCs) or monocyte-derived macrophages as effectors for ADCC and ADCP respectively. Human PBMCs were purified from leukapheresis of an anonymous healthy volunteer (HemaCare, VanNuys, Calif.) using Ficoll-Paque™ Plus density gradients (Amersham Biosciences, Newark, N.J.). Monocyte-derived macrophages were generated as described (Richards et al., 2008, Mol Cancer Ther 7[8]:2517-27). Purified PBMCs used in these assays were DNA genotyped for FcγRIIa (position 131) and FcγRIIIa (position 158) using methods by and as a commercial service at Gentris® Clinical Genetics (Morrisville, N.C.). For both sets of experiments donor allotypes were determined to be heterozygous for both FcγRIIa (H131/R131) and FcγRIIIa (V158/F158). ADCC was determined by lactate dehydrogenase release as described (Richards et al., 2008, Mol Cancer Ther 7[8]:2517-27), except that Ramos cells were used as targets (seeded at 10,000 per well) and effector cells were added at a 50:1 PBMC/target cell ratio. Macrophage ADCP was determined by flow cytometry as described (Richards et al., 2008, Mol Cancer Ther 7[8]:2517-27), except that Ramos cells were used as targets and labeled with CFSE (Guava® Technologies, Hayward, Calif.).

The results are shown in FIG. 6C-D (ADCC) and FIG. 6E-F (ADCP). For ADCC, it has been described that FcγRIIIa-expressing natural killer cells are the primary effectors (Richards et al., 2008, Mol Cancer Ther 7[8]:2517-27).

For macrophage phagocytosis, the FcγRIIa is the dominant receptor, with less prominent but still significant contributions from FcγRI and FcγRIIIa. The H268F/S324T variant had similar ADCC activity to native IgG1 and slightly improved ADCP (FIG. 6C,E). Combination with the AE and DE variants resulted in moderate (5.3-fold) and dramatic (22-fold) enhancements in ADCC activity, respectively, (FIGS. 6C and 7) as a consequence of their increased binding to FcγRIIIa (FIG. 9). The FT+AE and FT+DE variants also showed 4- to 5-fold improvements in macrophage ADCP (FIGS. 6E and 7), consistent with their greater binding to the activating receptors, particularly FcγRIIa (FIG. 9). The EFT variant, which has 70% reduced FcγRIIIa affinity (FIG. 9), mediated lower ADCC activity, both in terms of its potency and efficacy (FIGS. 6D and 7), and ADCP comparable to native IgG1 (FIGS. 6F and 7). Addition of the AE substitutions restored ADCC to IgG1 level (FIGS. 6D and 7). Interestingly, the EFT+AE combination did not enhance phagocytosis (FIGS. 6F and 7), despite its improved affinity for the activating receptors and particularly strong binding to FcγRIIa. This result may reflect a role of the inhibitory receptor FcγRIIb, which binds tightly to this variant, distinguishing this outcome from observations in previous work (Richards et al., 2008, Mol Cancer Ther 7[8]:2517-27). Regardless, together the variants provide a range of effector function activities, including dramatically improved complement-mediated yet preserved FcγR-mediated activities (EFT+AE), and simultaneously enhanced CDC, ADCC, and ADCP (FT+AE, FT+DE).

Figure 10:
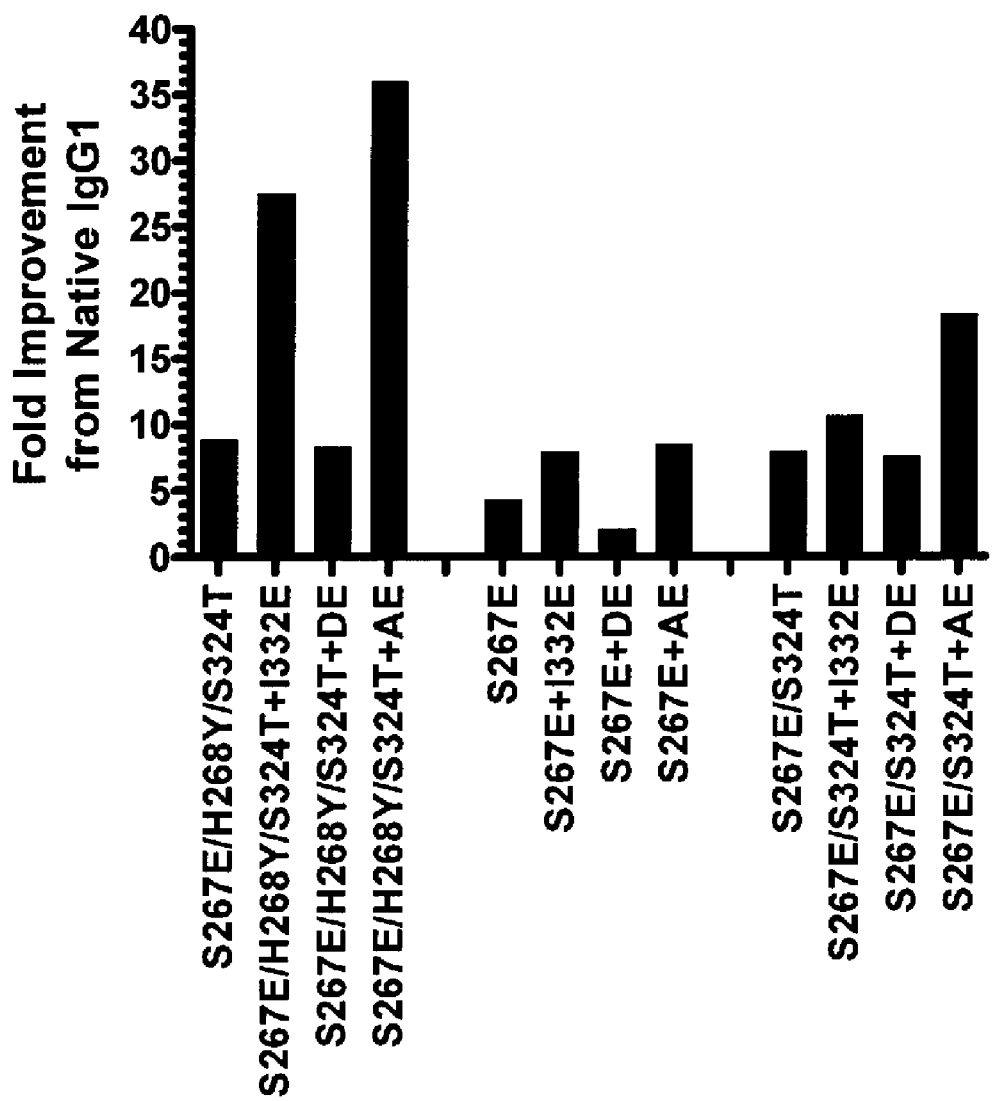
FIG. 10. CDC activity of additional Fc variant anti-CD20 mAbs against opsonized Ramos cells using human complement. Antibody-dependent % lysis was measured at multiple antibody concentrations by Alamar Blue®-based detection (mean±SE of duplicate wells), and EC$_{50}$ fold improvement compared to native IgG1 was calculated.

Additional variants were constructed by combining other CDC-enhancing substitutions with the AE and DE variants. These were expressed and screened in the context of ocrelizumab for CDC activity as described above. CDC results are shown in FIG. 10. Again, I332E and S267E were identified as a synergistic pair, and their synergy was absent in the presence of 239D.

Overall the different properties of the variant combinations illustrate the engineering challenge posed by the overlapping binding sites on the Fc region for C1q and FcγR. Two issues related to the interplay between complement and FcγR-mediated effector mechanisms include the dependence of CR activation on binding to pathogen-associated molecular patterns (PAMPs), (Gasque 2004, Mol Immunol 41[11]:1089-98) for example cell wall β-glucan (Vetvicka et al., 1996, J Clin Invest 98[1]:50-61; Vetvicka et al., 1997, J Immunol 159[2]:599-605; Yan et al., 1999, J Immunol 163[6]:3045-52), and the negative regulation of complement activation by CRPs (Zipfel et al., 2009, Nat Rev Immunol 9[10]:729-40), which include both soluble and cell surface proteins. Synergy between enhanced recruitment of complement and improved FcγR engagement may overcome these regulatory barriers for effector function against human tumors, eliciting a response similar to that against pathogens.

Example 3

Engineering of CDC-Enhanced Anti-CD19 and -CD40 Antibodies

In another experiment, the transferability of the variants to other antibodies was examined. The substitution combination with potent CDC enhancement, EFT+AE, was tested in the context of humanized anti-human CD19 and anti-human CD40 antibodies. Humanized, affinity-optimized 4G7 (Meeker et al., 1984, Hybridoma 3[4]:305-20) anti-human CD19 antibody and humanized S2C6 (Koho et al., 1984, Cancer Immunol Immunother 17[3]:165-72; Paulie et al., 1984, Cancer Immunol Immunother 17[3]:173-9) anti-human CD40 antibody were engineered as described (Lazar et al., 2007, Mol Immunol 44[8]:1986-98; Horton et al., 2008, Cancer Res 68[19]:8049-57). Fc variant versions of the anti-CD19 and CD40 antibodies were constructed by subcloning into the appropriate IgG1 and Cκ pTT5 vectors from ocrelizumab Fc variants. Antibodies were expressed and purified as described above.

Figure 11:
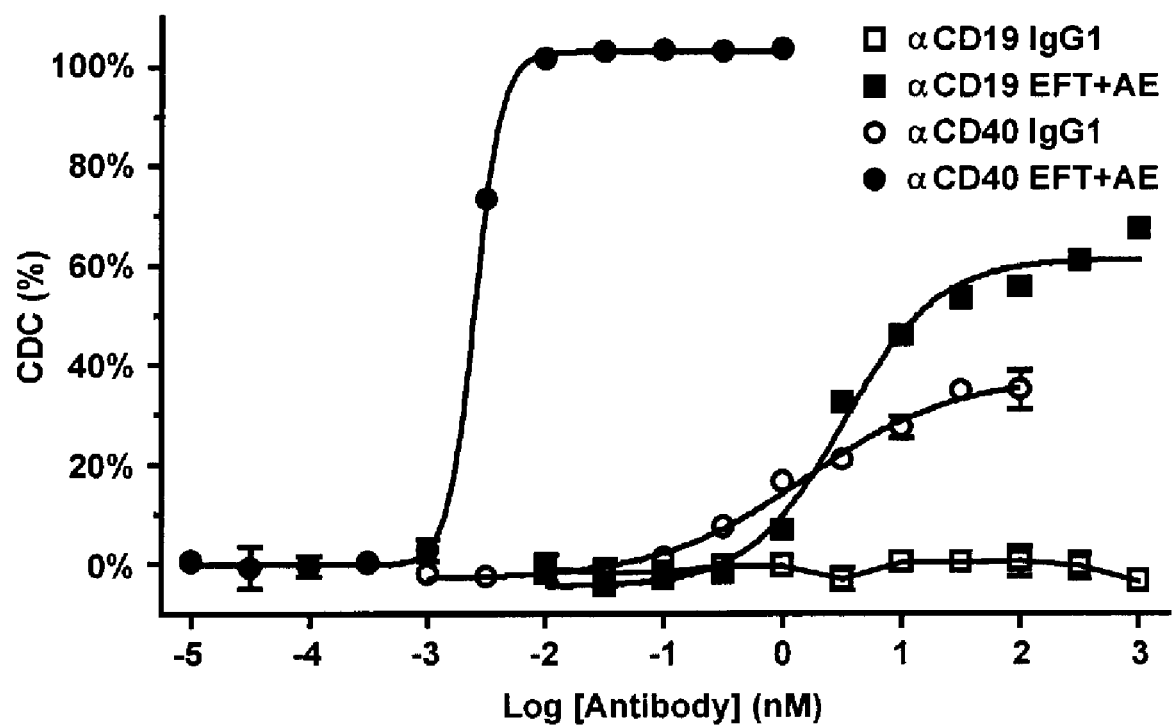
FIG. 11. EFT+AE variant enhances CDC in anti-CD19 and anti-CD40 mAbs. CDC activity of variant and IgG1 versions of humanized anti-CD19 and anti-CD40 antibodies was tested against Ramos cells using human complement. Antibody-dependent % lysis was measured at multiple antibody concentrations by Alamar Blue-based detection (mean±SE of duplicate wells).

Native IgG1 and CDC-enhanced variants were examined in the CDC assay against Ramos cells as described above. The Fc variant antibodies exhibited improved CDC activity, both in terms of potency and efficacy (FIG. 11), consistent with the anti-CD20 results. Strikingly, the variant anti-CD19 antibody mediated complement activity even though the native IgG1 version was completely lacking, reaching approximately 60% lysis with an $EC_{50}$ of 3.2 nM. The variant anti-CD40 showed remarkable gains in efficacy (2.5-fold) and potency (620-fold) relative to the native IgG1 version. Whereas most mAbs mediate ADCC in vitro, fewer seem capable of mediating complement activity. One possible reason for the high bar for complement activity is that it requires high antibody opsonization density (Dechant et al., 2008, Cancer Res 68[13]:4998-5003; Macor et al., 2007, Immunol Lett 111[1]:6-13; Spiridon et al., 2002, Clin Cancer Res 8[6]:1720-30), which is consistent with the fact that pentameric IgM is the most active isotype for complement. Overall these results demonstrate that the identified substitutions are not only broadly useful for anti-cancer antibodies, but can confer potent CDC activity even when it is absent or weak in a native IgG1.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

We claim:

1. An antibody comprising a variant Fc region of a parent Fc polypeptide, wherein said variant Fc region comprises substitutions at positions 267, 268, and 324, wherein said substitution at position 267 is glutamic acid, said substitution at position 268 is phenylalanine, and said substitution at position 324 is threonine, wherein numbering is according to the EU index as in Kabat.

2. The antibody of claim 1, wherein said antibody is selected from the group consisting of a human antibody, a humanized antibody, and a monoclonal antibody.

3. The antibody of claim 2, wherein said antibody is a monoclonal antibody.

4. The antibody of claim 1, wherein said antibody has specificity for an antigen selected from the group consisting of CD19, CD20, and CD40.

5. The antibody of claim 4, wherein said antibody has specificity for CD20.

6. An antibody comprising a variant Fc region of a parent Fc polypeptide, wherein said variant Fc region comprises substitutions at positions 267, 268, and 324, wherein said substitution at position 267 is glutamic acid, said substitution at position 268 is phenylalanine, and said substitution at position 324 is threonine, wherein numbering is according to the EU index as in Kabat, and wherein said variant Fc region exhibits greater complement dependent cytotoxicity as compared to said parent Fc polypeptide.

7. The antibody of claim 6, wherein said antibody is selected from the group consisting of a human antibody, a humanized antibody, and a monoclonal antibody.

8. The antibody of claim 7, wherein said antibody is a monoclonal antibody.

9. The antibody of claim 6, wherein said antibody has specificity for an antigen selected from the group consisting of CD19, CD20, and CD40.

10. The antibody of claim 9, wherein said antibody has specificity for CD20.

* * * * *